(12) United States Patent
Reubinoff et al.

(10) Patent No.: US 12,281,328 B2
(45) Date of Patent: Apr. 22, 2025

(54) PHOTORECEPTOR CELLS FOR THE TREATMENT OF RETINAL DISEASES

(71) Applicant: Hadasit Medical Research Services and Development Ltd., Jerusalem (IL)

(72) Inventors: Benjamin E. Reubinoff, Moshav Bar-Giora (IL); Masha Gorshtein, MaAle Adumim (IL); Hanita Khaner, Givon-HaChadasha (IL); Alex Obolensky, Jerusalem (IL); Eyal Banin, Jerusalem (IL)

(73) Assignee: Hadasit Medical Research Services and Development Ltd., Jerusalem (IL)

( * ) Notice: Subject to any disclaimer, the term of this patent is extended or adjusted under 35 U.S.C. 154(b) by 507 days.

(21) Appl. No.: 16/484,420

(22) PCT Filed: Feb. 8, 2018

(86) PCT No.: PCT/IL2018/050145
§ 371 (c)(1),
(2) Date: Aug. 7, 2019

(87) PCT Pub. No.: WO2018/146679
PCT Pub. Date: Aug. 16, 2018

(65) Prior Publication Data
US 2020/0032204 A1 Jan. 30, 2020

Related U.S. Application Data

(60) Provisional application No. 62/456,155, filed on Feb. 8, 2017.

(51) Int. Cl.
*C12N 5/0793* (2010.01)
*A61K 35/30* (2015.01)

(52) U.S. Cl.
CPC .............. *C12N 5/062* (2013.01); *A61K 35/30* (2013.01); *C12N 2500/30* (2013.01); *C12N 2501/105* (2013.01); *C12N 2501/115* (2013.01); *C12N 2501/998* (2013.01); *C12N 2506/02* (2013.01); *C12N 2506/45* (2013.01)

(58) Field of Classification Search
CPC ................ C12N 5/062; C12N 2500/30; C12N 2501/105; C12N 2501/115; C12N 2501/998; C12N 2506/02; C12N 2506/45; A61K 35/30
See application file for complete search history.

(56) References Cited

U.S. PATENT DOCUMENTS

| | | | |
|---|---|---|---|
| 3,791,932 A | 2/1974 | Schuurs et al. | |
| 3,839,153 A | 10/1974 | Schuurs et al. | |
| 3,850,578 A | 11/1974 | Mcconnell | |
| 3,850,752 A | 11/1974 | Schuurs et al. | |
| 3,853,987 A | 12/1974 | Dreyer | |
| 3,867,517 A | 2/1975 | Ling | |
| 3,879,262 A | 4/1975 | Schuurs et al. | |
| 3,901,654 A | 8/1975 | Gross | |
| 3,935,074 A | 1/1976 | Rubenstein et al. | |
| 3,984,533 A | 10/1976 | Uzgiris | |
| 3,996,345 A | 12/1976 | Ullman et al. | |
| 4,034,074 A | 7/1977 | Miles | |
| 4,098,876 A | 7/1978 | Piasio et al. | |
| 4,666,828 A | 5/1987 | Gusella | |
| 4,683,202 A | 7/1987 | Mullis | |
| 4,801,531 A | 1/1989 | Frossard | |
| 4,879,219 A | 11/1989 | Wands et al. | |
| 5,011,771 A | 4/1991 | Bellet et al. | |
| 5,192,659 A | 3/1993 | Simons | |
| 5,272,057 A | 12/1993 | Smulson et al. | |
| 5,281,521 A | 1/1994 | Trojanowski et al. | |
| 5,755,785 A | 5/1998 | Rowsey et al. | |
| 5,843,780 A | 12/1998 | Thomson | |
| 5,941,250 A | 8/1999 | Aramant et al. | |
| 5,962,027 A | 10/1999 | Hughes | |
| 6,045,791 A | 4/2000 | Liu | |
| 6,090,622 A | 7/2000 | Gearhart et al. | |
| 7,267,981 B2 | 9/2007 | Amit et al. | |
| 7,541,186 B2 | 6/2009 | Reh et al. | |
| 9,133,435 B2 | 9/2015 | Takahashi et al. | |
| 2004/0067580 A1 | 4/2004 | Amit et al. | |
| 2010/0105137 A1 | 4/2010 | Takahshi et al. | |
| 2011/0027333 A1 | 2/2011 | Idelson et al. | |
| 2011/0223140 A1 | 9/2011 | Park et al. | |
| 2013/0196369 A1 | 8/2013 | Hikita et al. | |
| 2015/0010922 A1* | 1/2015 | Reubinoff | G01N 33/56966 435/7.21 |
| 2015/0159134 A1 | 6/2015 | Choudhary et al. | |
| 2016/0243285 A1* | 8/2016 | Zhang | A61L 27/3834 |

(Continued)

FOREIGN PATENT DOCUMENTS

| | | |
|---|---|---|
| CA | 2856867 | 5/2013 |
| CN | 103627669 A | 3/2014 |
| EP | 2128244 A1 | 12/2009 |

(Continued)

OTHER PUBLICATIONS

Lamba et al ("Efficient generation of retinal progenitor cells from human embryonic stem cells," PNAS 103:34 Aug. 22, 2006).*
German et al ("Retinal pigment epithelial cells promote spatial reorganization and differentiation of retina photoreceptors," Journal of Neuroscience Research 86:3503-3514 (2008)).*
Idelson ("Directed Differentiation of Human Embryonic Stem Cells into Functional Retinal Pigment Epithelium Cell," Cell Stem Cell 5, 396-408, Oct. 2, 2009).*
Lamba et al ("Transplantation of Human Embryonic Stem Cell-Derived Photoreceptors Restores Some Visual Function in Crx-Deficient Mice," Cell Stem Cell 4, 73-79, Jan. 9, 2009) (Lamba).*
Santos-Ferreira ("Rebuilding the Missing Part-A Review on Photoreceptor Transplantation," Frontiers in Systems Neuroscience 10 Article 105 Jan. 2017).*
Lamba et al ("Generation, Purification and Transplantation of Photoreceptors Derived from Human Induced Pluripotent Stem Cells," PLos One 5(1) 2010).*

(Continued)

*Primary Examiner* — Emily A Cordas

(57) ABSTRACT

A method of generating photoreceptor cells is disclosed. Cell populations comprising photoreceptor cells and uses thereof are also disclosed.

10 Claims, 22 Drawing Sheets

(22 of 22 Drawing Sheet(s) Filed in Color)

(56) References Cited

U.S. PATENT DOCUMENTS

| | | | | |
|---|---|---|---|---|
| 2016/0345827 | A1* | 12/2016 | Palczewski | .......... A61B 3/1225 |
| 2018/0228846 | A1* | 8/2018 | Bohana-Kashtan | ... C12N 5/062 |

FOREIGN PATENT DOCUMENTS

| | | |
|---|---|---|
| EP | 2784152 | 10/2014 |
| EP | 3105320 A1 | 12/2016 |
| GB | 2327675 A | 2/1999 |
| WO | 01/55114 A1 | 8/2001 |
| WO | 02/060875 A1 | 8/2002 |
| WO | 03/068223 A1 | 8/2003 |
| WO | 03/068233 A1 | 8/2003 |
| WO | 2005/014549 A1 | 2/2005 |
| WO | 2006/040763 A2 | 4/2006 |
| WO | 2006/070370 A2 | 7/2006 |
| WO | WO 2007/100692 | 9/2007 |
| WO | WO 2011/055855 | 5/2011 |
| WO | WO 2015/054526 | 4/2015 |
| WO | 2015/121687 A1 | 8/2015 |
| WO | 2017/017686 A1 | 2/2017 |
| WO | 2017/021972 A1 | 2/2017 |
| WO | 2017/091844 A1 | 6/2017 |
| WO | 2018/146679 A2 | 8/2018 |

OTHER PUBLICATIONS

Brevini et al., No shortcuts to pig embryonic stem cells 2010, Theriogenology, vol. 74, pp. 544-550.*

Paris et al. ( Equine embryos and embryonic stem cells: Defining reliable markers of pluripotency2010, Theriogenology, vol. 74, pp. 516-524).*

Munoz et al. (Conventional pluripotency markers are unspecific for bovine embryonic-derived cell-lines2008, Theriogenology, vol. 69, pp. 1159-1164).*

Gomez et al. (Derivation of cat embryonic stem-like cells from in vitro-produced blastocysts on homologous and heterologous feeder cells2010, Theriogenology, vol. 74, pp. 498-515).*

Jean et al. (Pluripotent genes in avian stem cells2013, Develop. Growth Differ., vol. 55, pp. 41-51).*

Hong et al. (Derivation and Characterization of Embryonic Stem Cells Lines Derived from Transgenic Fischer 344 and Dark Agouti Rats2012, Stem Cells and Development, vol. 21(9), pp. 1571-1586).*

Hombach-Klonisch ("Adult stem cells and their trans-differentiation potential—perspectives and therapeutic applications," J Mol Med (2008) 86:1301-1314).*

Hill et al ("Dimethyl sulfoxide in the treatment of retinal disease;" Annals of the New York Academy of Sciences 243(1): 485-490 (1975)) (Hill). (Year: 1975).*

Zhong et al ("Generation of three-dimensional retinal tissue with functional photoreceptors from human iPSCs," Nature Communications 5:4047 2014) (Year: 2014).*

Verra et al ("Diurnal rodents as pertinent animal models of human retinal physiology and pathology," Progress in Retinal and Eye Research 74 (2020)), (Year: 2020).*

Xia et al. "An in vitro comparison of two different subpopulations of retinal progenitor cells for self-renewal and multipotentiality." Brain research 1433 (2012): 38-46. (Year: 2012).*

European Search Report issued in European Application No. 18750704.1, mailed on Sep. 8, 2020, 10 pages.

International Preliminary Report on Patentability issued in International Application No. PCT/IL18/50145, mailed on Aug. 22, 2019, 9 pages.

International Search Report and Written Opinion issued in International Application No. PCT/IL18/50145, mailed on Jul. 27, 2018, 11 pages.

Algvere et al. (Mar. 1997) "Transplantation of RPE in Age-related Macular Degeneration: Observations in Disciform Lesions and Dry RPE Atrophy", Graefe's Archive for Clinical and Experimental Ophthalmology, 235 (3):149-158.

Aoi et al. (Aug. 1, 2008) "Generation of Pluripotent Stem Cells From Adult Mouse Liver and Stomach Cells", American Association for the Advancement of Science, 321(5889):699-702.

Bigar et al. (Aug. 1992) "Corneal Transplantation", Current Opinion in Ophthalmology, 3(4):473-481.

Bongso et al. (Aug. 1989) "Improved Quality of Human Embryos when Co-Cultured with Human Ampullary Cells", Human Reproduction, 4(6):706-713.

Chacko et al. (Feb. 24, 2000) "Survival and Differentiation of Cultured Retinal Progenitors Transplanted in the Subretinal Space of the Rat", Biochemical and Biophysical Research Communications, 268(3):842-846.

Chung et al. (Feb. 7, 2008) "Human Embryonic Stem Cell Lines Generated without Embryo Destruction", Cell Stem Cell, 2(2):113-117.

Doetschman et al. (May 1988) "Establishment of Hamster Blastocyst-Derived Embryonic Stem (ES) Cells", Developmental Biology, 127(1):224-227.

Gardner et al. (Jan. 1998) "Culture and Transfer of Human Blastocysts Increases Implantation Rates and Reduces the Need for Multiple Embryo Transfers", Fertility and Sterility, 69(1):84-88.

Giles et al. (Oct. 1993) "Pluripotency of Cultured Rabbit Inner Cell Mass Cells Detected by Isozyme Analysis and Eye Pigmentation of Fetuses Following Injection into Blastocysts or Morulae", Molecular Reproduction and Development, 36(2): 130-138.

Graves et al. (Dec. 1993) "Derivation and Characterization of Putative Pluripotential Embryonic Stem Cells from Preimplantation Rabbit Embryos", Molecular Reproduction and Development, 36(4):424-433.

Gropp et al. (Feb. 2013) "Stable Genetic Modification of Human Embryonic Stem Cells by Lentiviral Vectors", Molecular Therapy, 7(2):281-287.

Iannaccone et al. (May 1994) "Pluripotent Embryonic Stem Cells from the Rat Are Capable of Producing Chimeras", Developmental Biology, 163(1):288-292.

Kalkan et al. (Dec. 2014) "Mapping the Route From Naive Pluripotency to Lineage Specification", Philosophical Transactions of the Royal Society B Biological Sciences, 20130540, 369(1657):10 pages.

Lamba et al. (Aug. 22, 2006) "Efficient Generation of Retinal Progenitor Cells from Human Embryonic Stem Cells", Proceedings of the National Academy of Sciences of the United States of America, 103(34):12769-12774.

Lamba et al. (Jan. 20, 2010) "Generation, Purification and Transplantation of Photoreceptors Derived from Human Induced Pluripotent Stem Cells", Plos One, e8763, 5(1):9 pages.

Li et al. (Apr. 9, 2013) "Multipotent Stem Cells Isolated From the Adult Mouse Retina are Capable of Producing Functional Photoreceptor Cells", Cell Research, 23(6):788-802.

Mitalipova et al. (2001) "Pluripotency of Bovine Embryonic Cell Line Derived from Precompacting Embryos", Cloning, 3(2):59-67.

Notarianni et al. (1991) "Derivation of Pluripotent, Embryonic Cell Lines from the Pig and Sheep", Journal of Reproduction and Fertility Supplement, 43:255-260.

Osakada et al. (Feb. 3, 2008) "Toward the Generation of Rod and Cone Photoreceptors from Mouse, Monkey and Human Embryonic Stem Cells", Nature Biotechnology, 26(2):215-224.

Park et al. (Feb. 2008) "Reprogramming of Human Somatic Cells to Pluripotency With Defined Factors", Nature, 451(7175):141-146.

Patel et al., "Indications for and Outcomes of Repeat Penetrating Keratoplasty, 1989-1995", Ophthalmology, Apr. 2000, 107(4):719-724.

Reubinoff et al. (Apr. 2000) "Embryonic Stem Cell Lines From Human Blastocysts: Somatic Differentiation in Vitro", Nature Biotechnology, 18(4):399-404.

Richards et al. (Sep. 2002) "Human Feeders Support Prolonged Undifferentiated Growth of Human Inner Cell Masses and Embryonic Stem Cells", Nature Biotechnology, 20(9):933-936.

Shamblott et al. (Nov. 1998) "Derivation of Pluripotent Stem Cells from Cultured Human Primordial Germ Cells", Proceedings of the National Academy of Sciences of the United States of America, 95(23):13726-13731.

(56) References Cited

OTHER PUBLICATIONS

Takahashi et al. (Nov. 30, 2007) "Induction of Pluripotent Stem Cells from Adult Human Fibroblasts by Defined Factors", Cell, 131(5):861-872.
Thomson et al. (Nov. 6, 1998) "Embryonic Stem Cell Lines Derived from Human Blastocysts", Science, 282 (5391):1145-1147.
Thomson et al. (Aug. 1995) "Isolation of a Primate Embryonic Stem Cell Line", Proceedings of the National Academy of Sciences of the United States of America, 92(17):7844-7848.
Thomson et al. (Aug. 1996) "Pluripotent Cell Lines Derived from Common Marmoset (*Callithrix jacchus*) Blastocysts", Biology of Reproduction, 55(2):254-259.
Thomson et al. (1998) "Primate Embryonic Stem Cells", Current Topics in Developmental Biology, 38:133-165.
Tsubota (Nov.-Dec. 1999) "Ocular Surface Management in Corneal Transplantation, A Review", Japanese Journal of Ophthalmology, 43(6):502-508.
Wheeler (1994) "Development and Validation of Swine Embryonic Stem Cells: A Review", Reproduction, Fertility and Development, 6(5):563-568.
Yamanaka (2007) "Strategies and New Developments in the Generation of Patient-specific Pluripotent Stem Cells", Cell Stem Cell, 1(1):39-49.
Oplinger et al. (Apr. 1998) "A Comparison of Corneal Autografts With Homografts", Ophthalmic Surgery, Lasers and Imaging Retina, 29(4):305-308.
Peyman et al. (Feb. 1991) "A Technique for Retinal Pigment Epithelium Transplantation for Age-related Macular Degeneration Secondary to Extensive Subfoveal Scarring", Ophthalmic Surgery, Lasers and Imaging Retina, 22 (2):102-108 (9 pages).
Burdon et al., (1995) "A Survey of Corneal Graft Practice in the United Kingdom", Eye, 9(Suppl.):6-12.
Database Genbank,"Fibroblast Growth Factor 2 Isoform 34 kDa [*Homo sapiens*]", GenBank Accession No. NP_001997.
Database Genbank,"Glycogen Synthase Kinase-3 Beta Isoform 1 [*Homo sapiens*]", GenBank Accession No. NP_002084.2.
Database Genbank,"Glycogen Synthase Kinase-3 beta Isoform 2 [*Homo sapiens*]", GenBank Accession No. NP_001139628.1.
Glycine. (Dec. 5, 2022) "HomeSupportMedia Formulation Components Molecular Weight Concentration (mg/L) mM Amino Acids Discover SARSCoV-2 variant research solutions to advance your development", 75.0 18.75 0.25 L-Alanine 89.0 4.45 0, 1-3(2 pages).
Communication Pursuant to Article 94(3) EPC Dated Dec. 9, 2022 From the European Patent Office Re. Application No. 18750704.1. (5 Pages).
Examination Report Dated Dec. 5, 2022 From the Australian Government, IP Australia Re. Application No. 2018217992. (5 Pages).
Examination Report Dated Nov. 9, 2023 From the Australian Government, IP Australia Re. Application No. 2018217992. (5 Pages).
Notification of Decision of Rejection Dated Jan. 6, 2024 From the State Intellectual Property Office of the People's Republic of China Re. Application No. 201880021741.4 and Its Translation Into English. (15 Pages).
Notification of Office Action and Search Report Dated Oct. 10, 2022 From the State Intellectual Property Office of the People's Republic of China Re. Application No. 201880021741.4 and Its Translation Into English. (20 Pages).
Notification of Office Action and Search Report Dated May 11, 2023 From the State Intellectual Property Office of the People's Republic of China Re. Application No. 201880021741.4 and Its Translation Into English. (15 Pages).
Office Action Dated Oct. 27, 2022 From the Israel Patent Office Re. Application No. 268357. (4 Pages).
Requisition by the Examiner Dated Mar. 27, 2024 From the Innovation, Science and Economic Development Canada, Canadian Intellectual Property Office Re. Application No. 3,052,872. (5 Pages).
Supplementary European Search Report and the European Search Opinion Dated Sep. 8, 2020 From the European Patent Office Re. Application No. 18750704.1. (10 Pages).
Ikeda et al. "Generation of Rx+/Pax6+ Neural Retinal Precursors From Embryonic Stem Cells", Proc. Natl. Acad. Sci. USA, PNAS, 102(32): 11331-11336, Aug. 9, 2005.
Inoue et al. "Subretinal Transplantation of Bone Marrow Mesenchymal Stem Cells Delays Retinal Degeneration in the RCS Rat Model of Retinal Degeneration", Experimental Eye Research, 85(2): 234-241, Available Online May 6, 2007.
Klassen et al. "Multipotent Retinal Progenitors Express Developmental Markers, Differentiate Into Retinal Neurons, and Preserve Light-Mediated Behavior", Investigative Ophthalmology & Visual Science, 45(11): 4167-4173, Nov. 2004.
MacLaren et al. "Retinal Repair by Transplantation of Photoreceptor Precursors", Nature, 444(7116): 203-207, Nov. 9, 2006.
ThermoFisher Scientific, ThermoFisher Scientific, XP093005007, Technical Resources, 11320-DMEM/F-12, p. 1-3, Dec. 5, 2022.

* cited by examiner

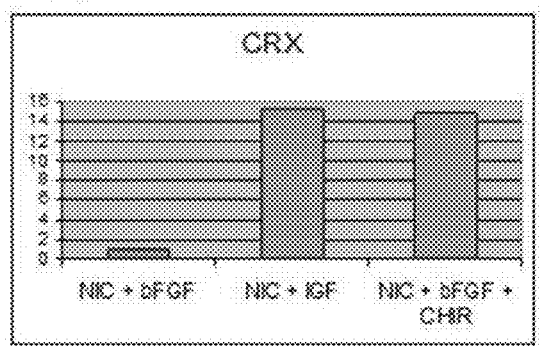 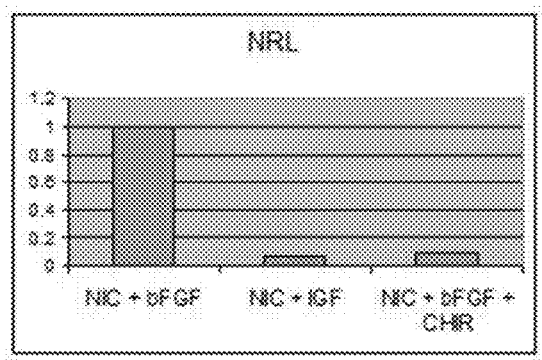
FIG. 7    FIG. 8
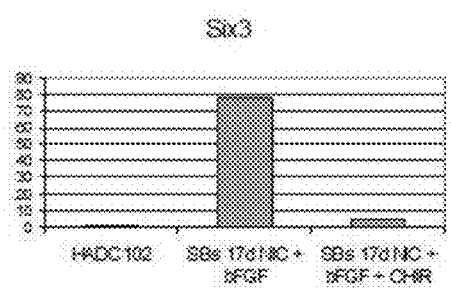 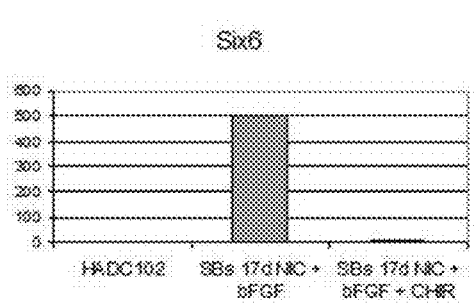
FIG. 9    FIG. 10

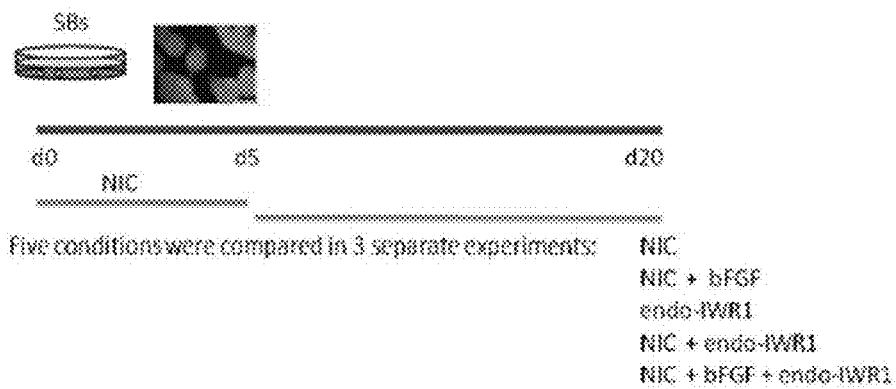
FIG. 15
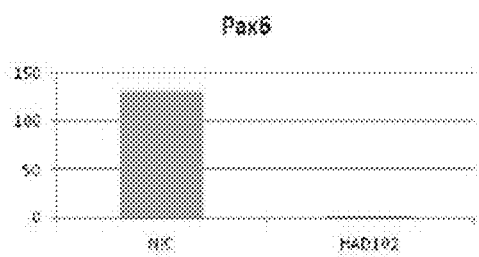
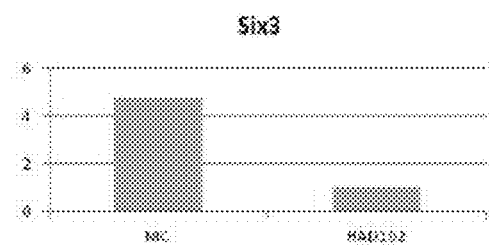
FIG. 16     FIG. 17

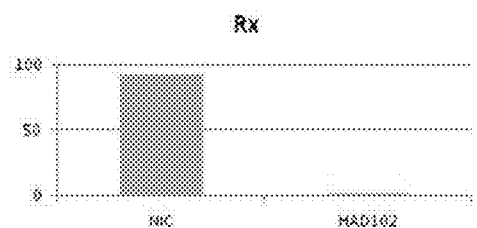
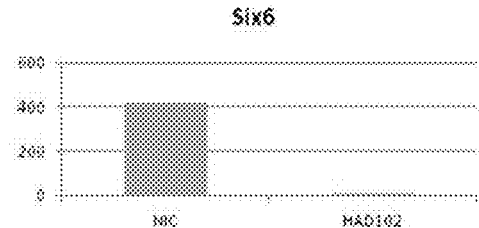
FIG. 18　　　　　　　　FIG. 19
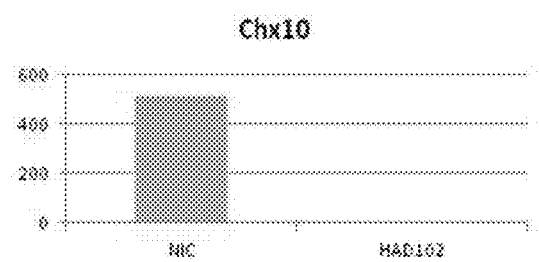
FIG. 20
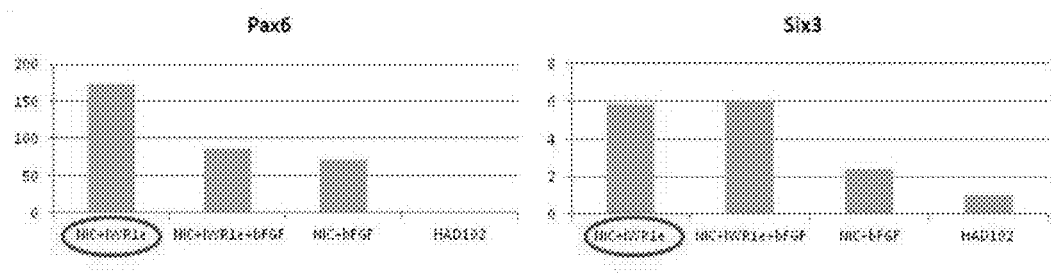
FIG. 21　　　　　　　　FIG. 22

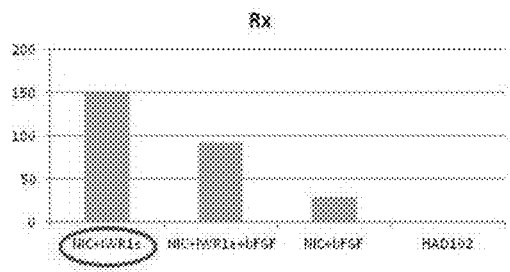
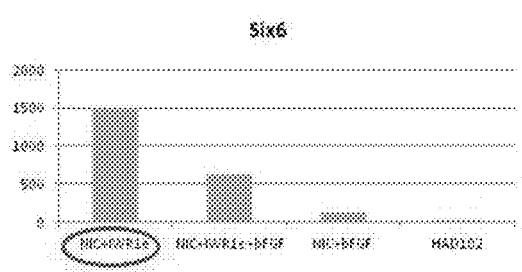
FIG. 23        FIG. 24
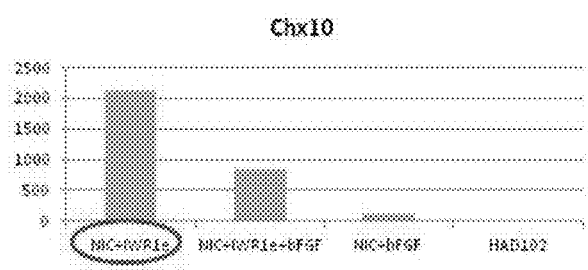
FIG. 25
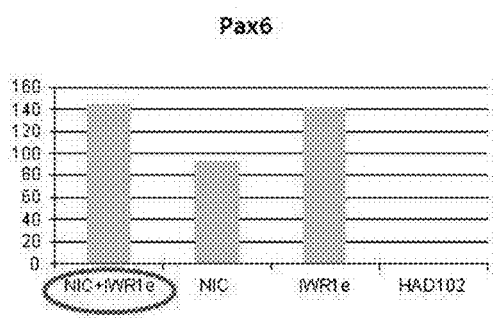
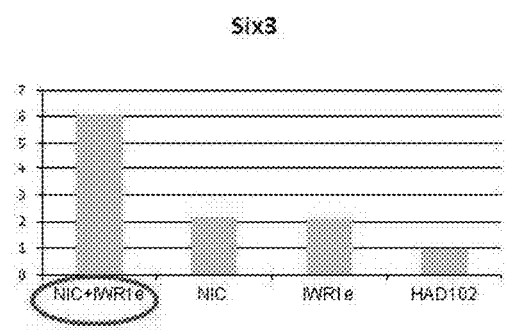
FIG. 26        FIG. 27

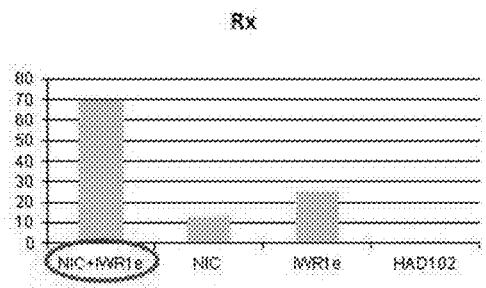
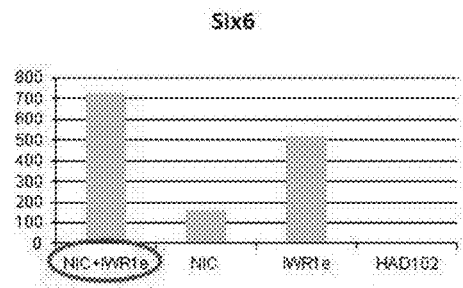
FIG. 28    FIG. 29
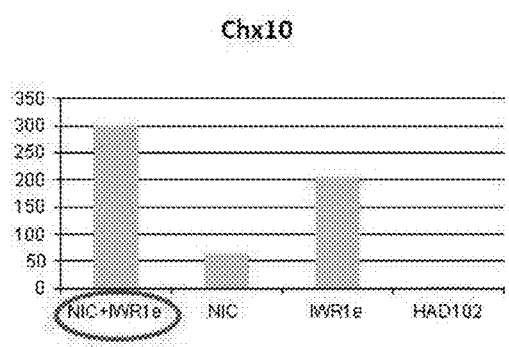
FIG. 30
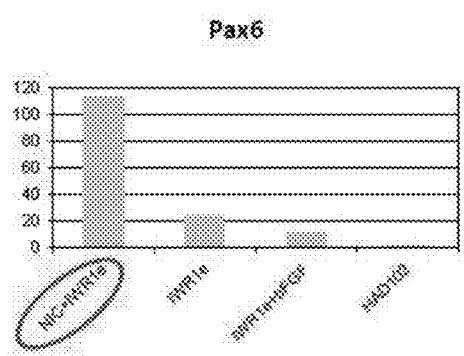
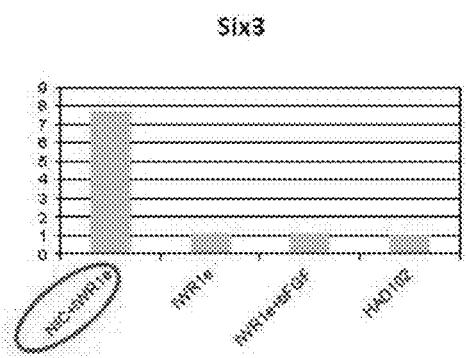
FIG. 31    FIG. 32

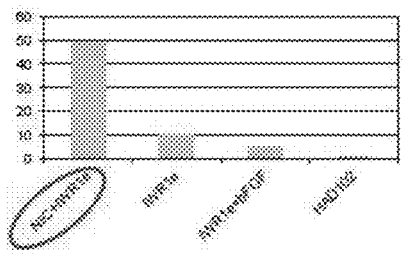 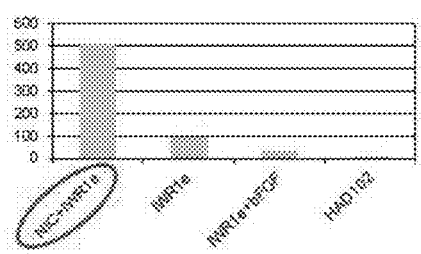
FIG. 33  FIG. 34
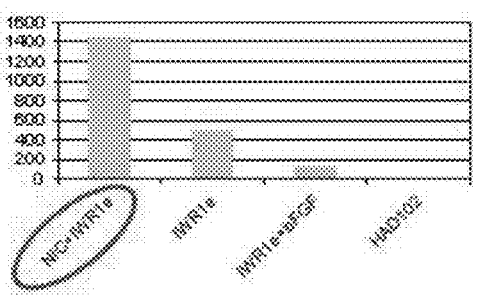
FIG. 35
FIG. 36

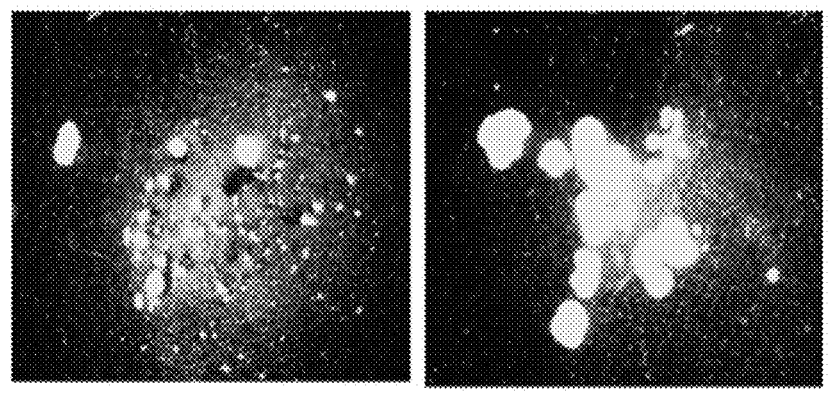
NIC+IWR1e      NIC + IWR1e + HSA
FIG. 37A      FIG. 37B
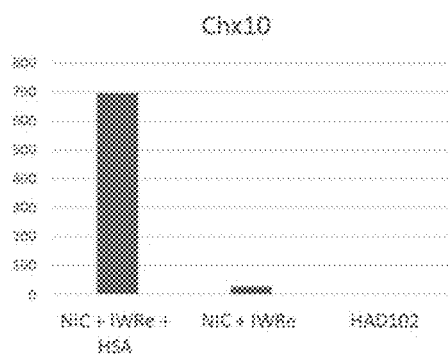
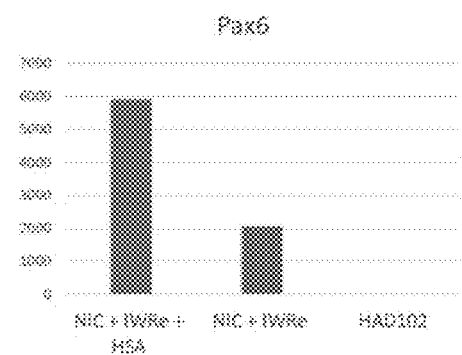
FIG. 38      FIG. 39

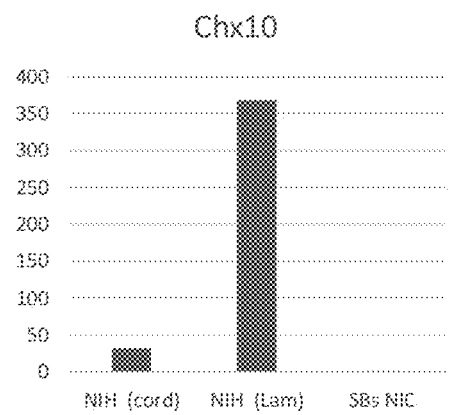
FIG. 54
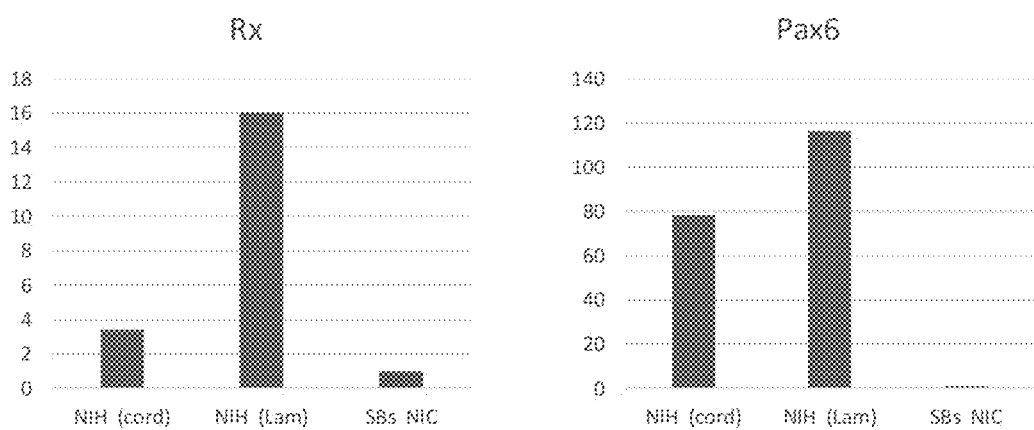
FIG. 55
FIG. 56

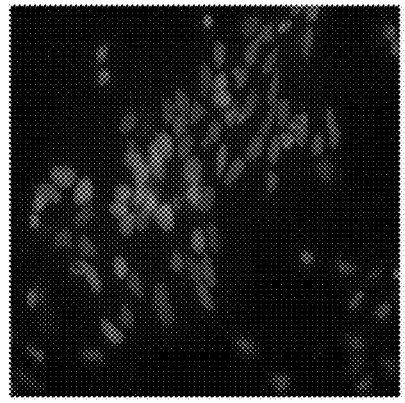 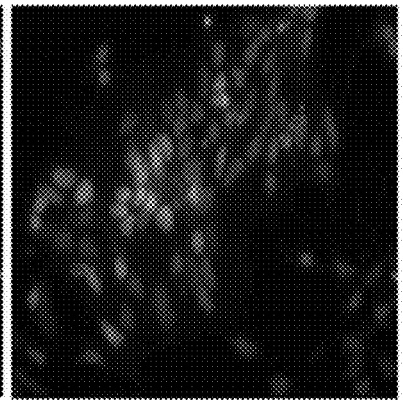
FIG. 60A  FIG. 60B
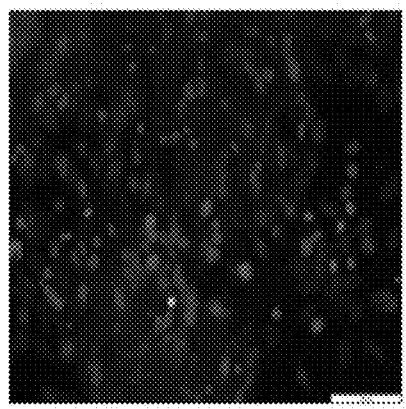 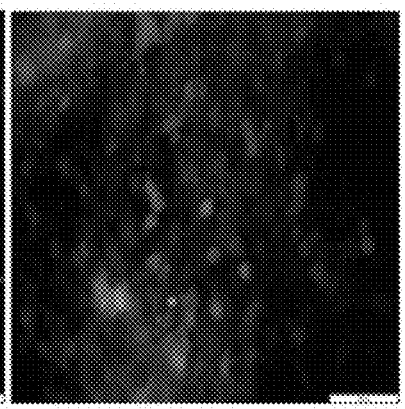
FIG. 61A  FIG. 61B

PHOTORECEPTOR CELLS FOR THE TREATMENT OF RETINAL DISEASES

CROSS-REFERENCE TO RELATED APPLICATIONS

This application is a National Phase Application of PCT/IL2018/050145, filed Feb. 8, 2018, which claims benefit under 35 USC § 119(e) to U.S. Provisional Application No. 62/456,155, filed Feb. 8, 2017, each of which are incorporated herein by reference in their entirety.

BACKGROUND

The present disclosure relates to methods of producing photoreceptor cells from pluripotent stem cells.

Retinal diseases often result in blindness due to loss of post-mitotic neuronal cells. Among the retinal diseases are rod or cone dystrophies, retinal degeneration, retinitis pigmentosa, diabetic retinopathy, macular degeneration, Leber congenital amaurosis and Stargardt disease. In most retinal degenerations, cell loss is primarily in the outer nuclear layer which includes rod and cone photoreceptors. With the loss of post-mitotic neuronal cell populations, an exogenous source of new cells as a replacement for photoreceptor cells is needed.

A potential replacement source of photoreceptor cells includes stem cells. Early studies incorporated the use of mouse cells, mouse stem cells or heterogeneous populations of retinal progenitor cells as a possible source of cells for replacement of lost photoreceptors. These early studies described transplantation of photoreceptor precursor cells from postnatal day 1 mouse retina, in vitro generation of retinal precursor cells from mouse embryonic stem cells, generation of retinal progenitor cells from postnatal day 1 mouse retinas, implantation of bone marrow mesenchymal stem cells in an RCS rat model of retinal degeneration, production of retinal progenitor cells, including ganglion cells, amacrine cells, photoreceptors wherein 0.01% of the total cells expressed S-opsin or rhodopsin, bipolar cells and horizontal cells, from the H1 human embryonic stem cell line (Lamba et al. Proc. Natl. Acad. Sci. 10(34):12769-12774, 2006) and induction of induced pluripotent stem cells (iPS) from human fibroblasts to produce retinal progenitor cells (Lamba et al. PLoS ONE 5(1):e8763. doi: 10.1371/journal.pone.0008763).

However, new methods that are more efficient for generating transplantable photoreceptor cells useful in cell therapy are needed. More specifically, methods that can generate photoreceptor progenitor cells that can efficiently produce both rods and cones photoreceptors are needed.

The present disclosure addresses these and other shortcomings in the field of regenerative medicine and photoreceptor cell therapy.

SUMMARY

According to an aspect of the present invention there is provided a method of treating a retinal disease in a subject in need thereof comprising:
(a) culturing a population of human pluripotent stem cells in a medium comprising at least 0.5 mM nicotinamide to obtain differentiating cells;
(b) culturing the differentiating cells in a medium which comprises at least one agent selected from the group consisting of a Wnt inhibitor, HSA, bFGF, IGF and a GSK3 inhibitor to generate photoreceptor cells; and
(c) administering a therapeutically effective amount of the photoreceptor cells to the subject, thereby treating the retinal disease.

The photoreceptor cells may be rods or cones or both rods and cones.

According to an aspect of the present invention there is provided a method of generating photoreceptor cells comprising:
(a) culturing a population of human pluripotent stem cells in a medium comprising at least 0.5 mM nicotinamide to obtain differentiating cells; and
(b) culturing the differentiating cells in a medium which comprises at least one agent selected from the group consisting of a GSK3 inhibitor, a Wnt inhibitor, bFGF, HSA, IGF to generate photoreceptor cells; and
(c) isolating the photoreceptor cells, thereby generating the photoreceptor cells.

According to embodiments of the present invention, the method further comprises isolating the photoreceptors following the culturing of step (b) and prior to the administering.

According to embodiments of the present invention, the method further comprises expanding the photoreceptor cells following the culturing of step (b).

According to embodiments of the present invention, the culturing of step (a) is effected under non-adherent conditions.

According to embodiments of the present invention, the culturing of step (b) is effected under non-adherent conditions.

According to embodiments of the present invention, the medium of step (b) comprises:
(i) nicotinamide and Wnt inhibitor;
(i) nicotinamide and bFGF;
(ii) nicotinamide and IGF;
(iii) nicotinamide, IGF and a GSK3 inhibitor; or
(v) nicotinamide, bFGF and Wnt inhibitor
(vi) nicotinamide, Wnt inhibitor and HSA
(vii) nicotinamide, bFGF, and HSA
(viii) nicotinamide, bFGF, Wnt inhibitor and HSA
(ix) nicotinamide, and HSA According to embodiments of the present invention, the culturing of step (a) is effected for at least 3 days.

According to embodiments of the present invention, the culturing of step (b) is effected for at least one week.

According to embodiments of the present invention, the medium of step (b) is devoid of activin A.

According to embodiments of the present invention, the medium of step (b) is devoid of a member of the TGFβ superfamily.

According to embodiments of the present invention, the method is effected in the absence of a member of the TGFbeta superfamily which allows differentiation into the photoreceptor cells.

According to embodiments of the present invention, the human pluripotent stem cells are cultured in a feeder cell conditioned medium prior to the culturing of step (a).

According to embodiments of the present invention, the human pluripotent stem cells are cultured in a feeder-free culture system on laminin prior to the culturing of step (a).

According to embodiments of the present invention, the method further comprises cryopreserving the photoreceptor cells following step (b) and prior to step (c).

According to embodiments of the present invention, the method further comprises cryopreserving the photoreceptor cells following step (c).

According to embodiments of the present invention, the cryopreserving is effected in a medium selected from the group consisting of 90% Human Serum/10% DMSO, CRYOSTOR™ 10%, CRYOSTOR™ 5%, CRYOSTOR™ 2%, STEM-CELLBANKER™ and PRIME-XV™ FreezIS.

According to embodiments of the present invention, the human pluripotent stem cells comprise human embryonic stem cells (ESCs) or induced pluripotent stem cells (iPSCs).

According to embodiments of the present invention, the medium of step (a) is devoid of Wnt inhibitor, bFGF, HSA, IGF and/or GSK3 inhibitor.

According to embodiments of the present invention, the GSK3 inhibitor comprises CHIR.

According to embodiments of the present invention, the Wnt inhibitor comprises endo-IWR1.

According to embodiments of the present invention, the non-adherent conditions comprise a non-adherent culture plate.

According to embodiments of the present invention, the non-adherent conditions comprise a non-adherent substrate.

According to embodiments of the present invention, the feeder cell conditioned medium comprises human cord fibroblast conditioned medium.

According to embodiments of the present invention, the transplanting is effected at the subretinal space of the eye.

According to embodiments of the present invention, the photoreceptor cells are transplanted in a suspension, or as a monolayer of cells immobilized on a matrix or a substrate.

According to an aspect of the present invention there is provided a method of generating photoreceptor cells comprising:

(a) culturing a population of human pluripotent stem cells in a medium comprising at least 0.5 mM nicotinamide, wherein the culture does not comprise any member of the TGFβ superfamily at a concentration which allows differentiation into the photoreceptor cells; and (b) isolating the photoreceptor cells from retinal pigmented epithelial (RPE) cells, thereby generating the photoreceptors.

According to an aspect of the present invention there is provided a population of photoreceptor cells obtainable according to the method as described herein.

According to embodiments of the present invention, the retinal disease or disorder is selected from at least one of retinitis pigmentosa, lebers congenital amaurosis, hereditary or acquired macular degeneration, age related macular degeneration (AMD), Best disease, retinal detachment, gyrate atrophy, choroideremia, pattern dystrophy, RPE dystrophies, Stargardt disease, RPE and retinal damage due to damage caused by any one of photic, laser, inflammatory, infectious, radiation, neovascular or traumatic injury.

According to an aspect of the present invention there is provided a method of treating a retinal disease or disorder in a subject in need thereof comprising administering a therapeutically effective amount of the population of photoreceptor cells as described herein to the subject thereby treating the retinal disease or disorder.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how different embodiments may be practiced.

In the drawings:

FIG. 1 is a schematic representation of a method of generating spheroid bodies (SBs) according to certain embodiments.

FIG. 2 is a schematic diagram of methods of generating photoreceptor progenitor cells by culturing SBs using different combinations of factors and timelines.

FIG. 3 is a graph illustrating expression of the eye field and retinal progenitor marker, Six3, by SBs that were cultured with combinations of NIC, bFGF, CHIR and IGF1 for 1 month.

FIG. 4 is a graph illustrating expression of the eye field and retinal progenitor marker, Six6, by SBs that were treated with combinations of NIC, bFGF, CHIR and IGF1 for 1 month.

FIG. 5 is a graph illustrating expression of the retinal progenitor marker, Chx10, by SBs that were treated with combinations of NIC, bFGF, CHIR and IGF1 for 1 month.

FIG. 6 is a graph illustrating expression of the eye field and retinal progenitor marker, Rx, by SBs that were treated with combinations of NIC, bFGF, CHIR and IGF1 for 1 month.

FIG. 7 is a graph illustrating expression of the photoreceptor progenitor and photoreceptor cells marker, CRX, by SBs that were treated with combinations of NIC, bFGF, CHIR and IGF1 for 1 month.

FIG. 8 is a graph illustrating expression of the photoreceptor progenitor and photoreceptor cells marker, NRL, by SBs that were treated with combinations of NIC, bFGF, CHIR and IGF1 for 1 month.

FIG. 9 is a graph illustrating the marker expression of Six3 by SBs cultured in NIC+bFGF or NIC+bFGF+CHIR for 17 days, and the control, HADC102, (undifferentiated HAD-C102 cells cultured for 6-7 days in NUTRISTEM® hPSC XF*Xeno-free medium for Human Pluripotent Stem Cells (Biological Industries).

FIG. 10 is a graph illustrating the marker expression of Six6 by SBs cultured in NIC+bFGF or NIC+bFGF+CHIR for 17 days, and the control, HADC102 (undifferentiated HAD-C102 cells cultured in NUTRISTEM® hPSC XF*Xeno-free medium.

FIG. 11 is a graph illustrating the marker expression of Chx10 by SBs cultured in NIC+bFGF or NIC+bFGF+CHIR for 17 days, and the control, HADC102 (undifferentiated HAD-C102 cells cultured in NUTRISTEM® hPSC XF*Xeno-free medium.

Figure 12:
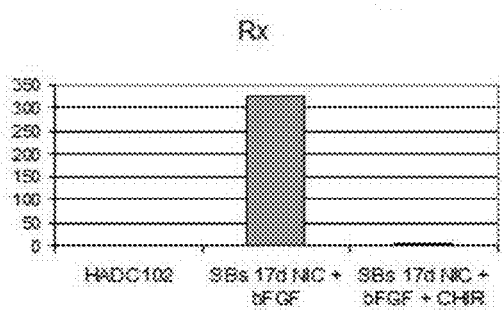

FIG. 12 is a graph illustrating the marker expression of Rx by SBs cultured in NIC+bFGF or NIC+bFGF+CHIR for 17 days, and the control, HADC102 (undifferentiated HAD-® cells cultured in NUTRISTEM® hPSC XF*Xeno-free medium.

Figure 13:
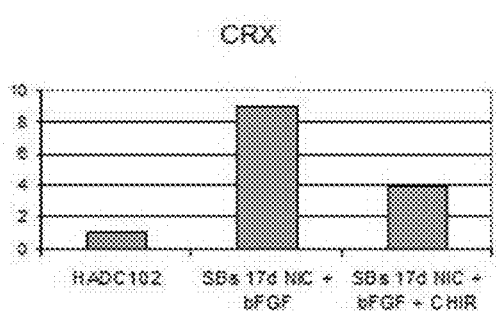

FIG. 13 is a graph illustrating the marker expression of CRX by SBs cultured in NIC+bFGF or NIC+bFGF+CHIR for 17 days, and the control, HADC102 (undifferentiated HAD-C102 cells cultured in NUTRISTEM® hPSC XF*Xeno-free medium.

Figure 14:
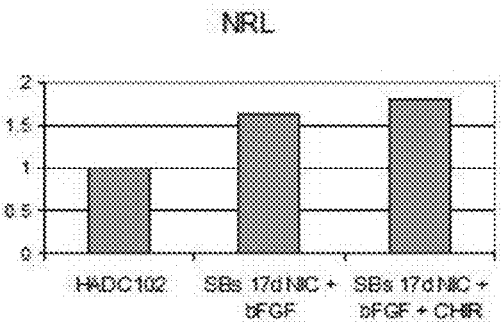

FIG. 14 is a graph illustrating the marker expression of NRL by SBs cultured in NIC+bFGF or NIC+bFGF+CHIR for 17 days, and the control, HADC102 (undifferentiated HAD-C102 cells cultured in NUTRISTEM® hPSC XF*Xeno-free medium.

FIG. 15 is a schematic drawing of different methods of culturing SBs, according to certain embodiments.

FIG. 16 is a graph illustrating expression of the marker, Pax6, by SBs that were cultured in NIC for 20 days. The control, HAD102, comprised undifferentiated cells from the cell line, HAD-C102, cultured in NUTRISTEM® hPSC XF*Xeno-free medium for Human Pluripotent Stem Cells (Cat #05-100-1A, Biological Industries).

FIG. 17 is a graph illustrating expression of the marker, Six3, by SBs that were cultured in NIC for 20 days, and the control, HAD102 (undifferentiated HAD-C102 cells cultured in NUTRISTEM® hPSC XF*Xeno-free medium).

FIG. 18 is a graph illustrating expression of the marker, Rx, by SBs that were cultured in NIC for 20 days, and the control, HAD102 (undifferentiated HAD-C102 cells cultured in NUTRISTEM® hPSC XF*Xeno-free medium).

FIG. 19 is a graph illustrating expression of the marker, Six6, by SBs that were cultured in NIC for 20 days, and the control, HAD102 (undifferentiated HAD-C102 cells cultured in NUTRISTEM® hPSC XF*Xeno-free medium).

FIG. 20 is a graph illustrating expression of the marker, Chx10, by SBs that were cultured in NIC for 20 days, and the control, HAD102 (undifferentiated HAD-C102 cells cultured in NUTRISTEM® hPSC XF*Xeno-free medium).

FIG. 21 is a graph illustrating expression of the marker, Pax6, by SBs that were cultured in either NIC+IWR1e or NIC+IWR1e+bFGF or NIC+bFGF for 20 days, and the control, HAD102 (undifferentiated HAD-C102 cells cultured in NUTRISTEM® hPSC XF*Xeno-free medium).

FIG. 22 is a graph illustrating expression of the marker, Six3, by SBs that were cultured in either NIC+IWR1e or NIC+IWR1e+bFGF or NIC+bFGF for 20 days, and the control, HAD102 (undifferentiated HAD-C102 cells cultured in NUTRISTEM® hPSC XF*Xeno-free medium).

FIG. 23 is a graph illustrating expression of the marker, Rx, by SBs that were cultured in either NIC+IWR1e or NIC+IWR1e+bFGF or NIC+bFGF for 20 days, and the control, HAD102 (undifferentiated HAD-C102 cells cultured in NUTRISTEM® hPSC XF*Xeno-free medium).

FIG. 24 is a graph illustrating expression of the marker, Six6, by SBs that were cultured in either NIC+IWR1e or NIC+IWR1e+bFGF or NIC+bFGF for 20 days, and the control, HAD102 (undifferentiated HAD-C102 cells cultured in NUTRISTEM® hPSC XF*Xeno-free medium).

FIG. 25 is a graph illustrating expression of the marker, Chx10, by SBs that were cultured in either NIC+IWR1e or NIC+IWR1e+bFGF or NIC+bFGF for 20 days, and the control, HAD102 (undifferentiated HAD-C102 cells cultured in NUTRISTEM® hPSC XF*Xeno-free medium).

FIG. 26 is a graph illustrating expression of the marker, Pax6, by SBs that were cultured in either NIC+IWR1e or NIC or IWR1e, and the control, HAD102 (undifferentiated HAD-C102 cells cultured in NUTRISTEM® hPSC XF*Xeno-free medium).

FIG. 27 is a graph illustrating expression of the marker, Six3, by SBs that were cultured in either NIC+IWR1e or NIC or IWR1e, and the control, HAD102 (undifferentiated HAD-C102 cells cultured in NUTRISTEM® hPSC XF*Xeno-free medium.

FIG. 28 is a graph illustrating expression of the marker, Rx, by SBs that were cultured in either NIC+IWR1e or NIC or IWR1e, and the control, HAD102 (undifferentiated HAD-C102 cells cultured in NUTRISTEM® hPSC XF*Xeno-free medium).

FIG. 29 is a graph illustrating expression of the marker, Six6, by SBs that were cultured in either NIC+IWR1e or NIC or IWR1e, and the control, HAD102 (undifferentiated HAD-C102 cells cultured in NUTRISTEM® hPSC XF*Xeno-free medium).

FIG. 30 is a graph illustrating expression of the marker, Chx10, by SBs that were cultured in either NIC+IWR1e or NIC or IWR1e, and the control, HAD102 (undifferentiated HAD-C102 cells cultured in NUTRISTEM® hPSC XF*Xeno-free medium).

FIG. 31 is a graph illustrating expression of the marker, Pax6, by SBs that were cultured in either NIC+IWR1e or IWR1e or IWR1e+bFGF, and the control, HAD102 (undifferentiated HAD-C102 cells cultured in NUTRISTEM® hPSC XF*Xeno-free medium).

FIG. 32 is a graph illustrating expression of the marker, Six3, by SBs that were cultured in either NIC+IWR1e or IWR1e or IWR1e+bFGF, and the control, HAD102 (undifferentiated HAD-C102 cells cultured in NUTRISTEM® hPSC XF*Xeno-free medium).

FIG. 33 is a graph illustrating expression of the marker, Rx, by SBs that were cultured in either NIC+IWR1e or IWR1e or IWR1e+bFGF, and the control, HAD102 (undifferentiated HAD-C102 cells cultured in NUTRISTEM® hPSC XF*Xeno-free medium).

FIG. 34 is a graph illustrating expression of the marker, Six6, by SBs that were cultured in either NIC+IWR1e or IWR1e or IWR1e+bFGF, and the control, HAD102 (undifferentiated HAD-C102 cells cultured in NUTRISTEM® hPSC XF*Xeno-free medium).

FIG. 35 is a graph illustrating expression of the marker, Chx10, by SBs that were cultured in either NIC+IWR1e or IWR1e or IWR1e+bFGF, and the control, HAD102 (undifferentiated HAD-C102 cells cultured in NUTRISTEM® hPSC XF*Xeno-free medium).

FIG. 36 is a schematic diagram of different methods of culturing SBs with various combinations of agents, including human serum albumin (HSA).

FIG. 37A is an image of hESC-derived SBs cultured with NIC+IWR1e.

FIG. 37B is an image of hESC-derived SBs cultured with NIC+IWR1e+HSA.

FIG. 38 is a graph illustrating the expression of the marker, Chx10, by SBs after they were cultured in either NIC+IWRe+HSA or NIC+IWRe for 4 weeks, and the control, HAD102 (undifferentiated HAD-C102 cells cultured in NUTRISTEM® hPSC XF*Xeno-free medium).

FIG. 39 is a graph illustrating the expression of the marker, Pax6, by SBs after they were cultured in either NIC+IWRe+HSA or NIC+IWRe for 4 weeks, and the control, HAD102 (undifferentiated HAD-C102 cells cultured in NUTRISTEM® hPSC XF*Xeno-free medium).

Figure 40:
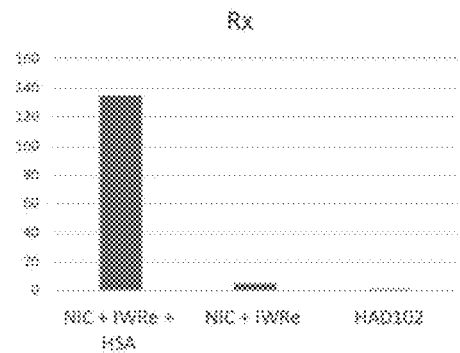

FIG. 40 is a graph illustrating the expression of the marker, Rx, by SBs after they were cultured in either NIC+IWRe+HSA or NIC+IWRe for 4 weeks, and the control, HAD102 (undifferentiated HAD-C102 cells cultured in NUTRISTEM® hPSC XF*Xeno-free medium).

Figure 41:
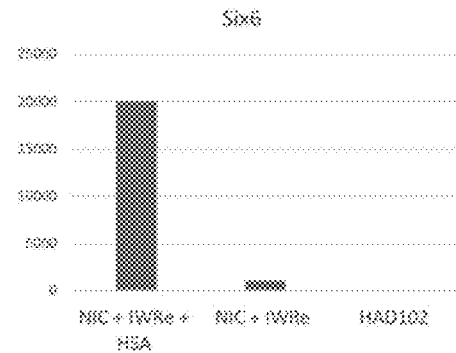

FIG. 41 is a graph illustrating the expression of the marker, Six6, by SBs after they were cultured in either NIC+IWRe+HSA or NIC+IWRe for 4 weeks, and the control, HAD102 (undifferentiated HAD-C102 cells cultured in NUTRISTEM® hPSC XF*Xeno-free medium).

Figure 42:
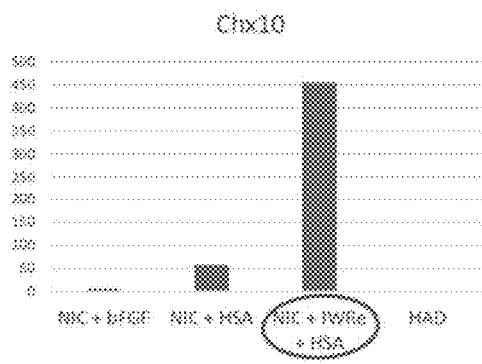

FIG. 42 is a graph illustrating the expression of the marker, Chx10, by SBs that were cultured in either NIC+bFGF or NIC+HSA or NIC+IWRe+HSA for 4 weeks, and the control, HAD (undifferentiated HAD-C102 cells cultured in NUTRISTEM® hPSC XF*Xeno-free medium).

Figure 43:
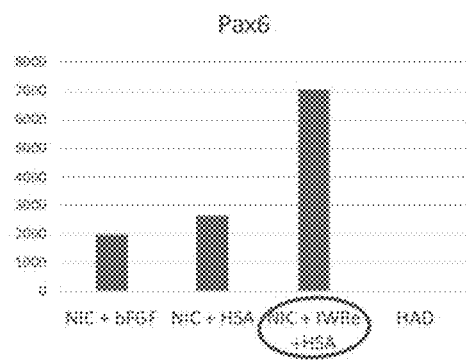

FIG. 43 is a graph illustrating the expression of the marker, Pax6, by SBs that were cultured in either NIC+bFGF or NIC+HSA or NIC+IWRe+HSA for 4 weeks, and the control, HAD (undifferentiated HAD-C102 cells cultured in NUTRISTEM® hPSC XF*Xeno-free medium).

Figure 44:
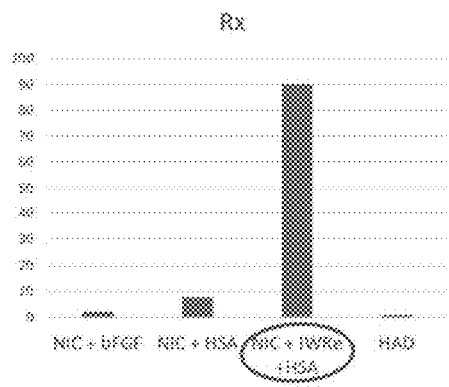

FIG. 44 is a graph illustrating the expression of the marker, Rx, by SBs that were cultured in either NIC+bFGF or NIC+HSA or NIC+IWRe+HSA for 4 weeks, and the control, HAD (undifferentiated HAD-C102 cells cultured in NUTRISTEM® hPSC XF*Xeno-free medium).

Figure 45:
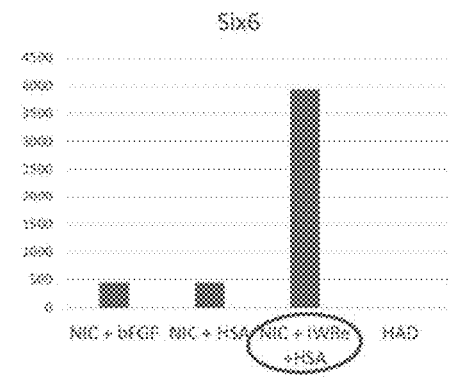

FIG. 45 is a graph illustrating the expression of the marker, Six6, by SBs that were cultured in either NIC+bFGF or NIC+HSA or NIC+IWRe+HSA for 4 weeks, and the control, HAD (undifferentiated HAD-C102 cells cultured in NUTRISTEM® hPSC XF*Xeno-free medium).

Figure 46:
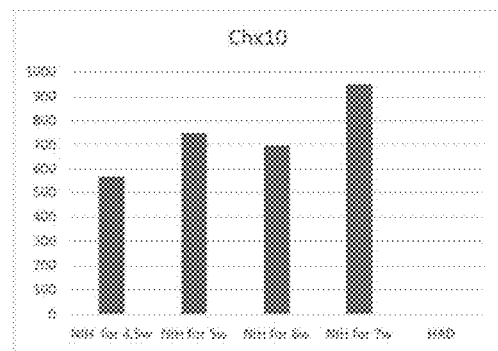

FIG. 46 is a graph illustrating the expression the marker, Chx10, by SBs that were cultured in either NIH (NIC, IWRe and HSA) for 4.5 weeks or NIH for 5 weeks or NIH for 6 weeks or NIH for 7 weeks, and the control, HAD (undifferentiated HAD-C102 cells cultured in NUTRISTEM® hPSC XF*Xeno-free medium).

Figure 47:
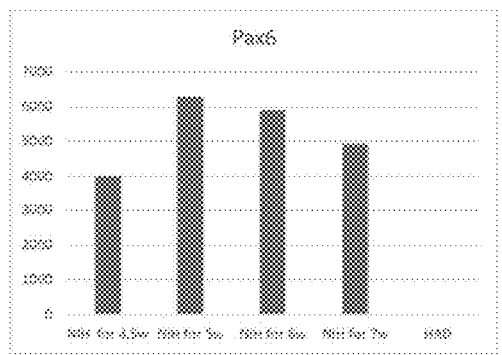

FIG. 47 is a graph illustrating the expression the marker, Pax6, by SBs that were cultured in either NIH for 4.5 weeks or NIH for 5 weeks or NIH for 6 weeks or NIH for 7 weeks, and the control, HAD (undifferentiated HAD-C102 cells cultured in NUTRISTEM® hPSC XF*Xeno-free medium).

Figure 48:
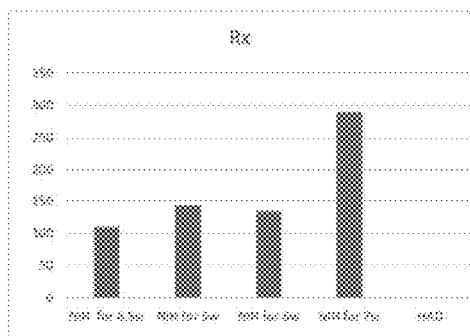

FIG. 48 is a graph illustrating the expression the marker, Rx, by SBs that were cultured in either NIH for 4.5 weeks or NIH for 5 weeks or NIH for 6 weeks or NIH for 7 weeks, and the control, HAD (undifferentiated HAD-C102 cells cultured in NUTRISTEM® hPSC XF*Xeno-free medium).

Figure 49:
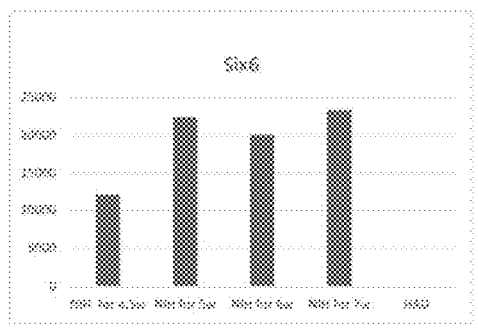

FIG. 49 is a graph illustrating the expression the marker, Six6, by SBs that were cultured in either NIH for 4.5 weeks or NIH for 5 weeks or NIH for 6 weeks or NIH for 7 weeks, and the control, HAD (undifferentiated HAD-C102 cells cultured in NUTRISTEM® hPSC XF*Xeno-free medium).

Figure 50:
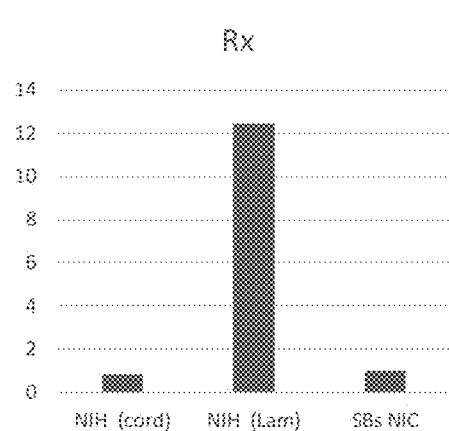

FIG. 50 is a graph illustrating the expression of the marker, Rx, by SBs that were derived from hESCs (HAD-C102) cultured on gelatin in NUTRISTEM® hPSC XF*Xeno-free medium conditioned by cord-feeders, and SBs that were cultured in suspension in NIH (NIC, IWRe and HSA) (NIH cord), compared to expression by SBs derived from hESCs cultured on laminin 521 in NUTRISTEM® hPSC XF*Xeno-free medium which were cultured in suspension in NIH (NIH Lam). The control used was SBs cultured in suspension overnight in the presence of NIC (SBs NIC).

Figure 51:
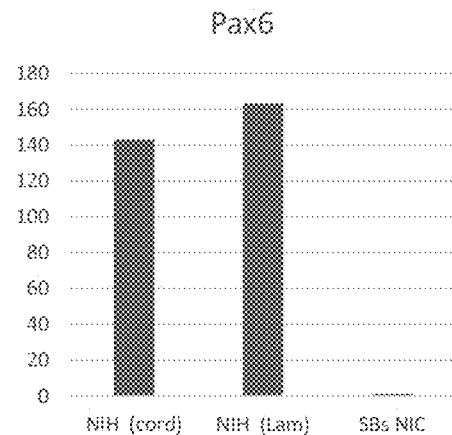

FIG. 51 is a graph illustrating the expression of the marker, Pax6, by SBs that were derived from hESCs cultured on gelatin in NUTRISTEM® hPSC XF*Xeno-free medium conditioned by Cord-feeders and that were cultured in suspension in NIH (NIH cord) compared to expression by SBs derived from hESCs cultured on laminin 521 in NUTRISTEM® hPSC XF*Xeno-free medium which were cultured in suspension in NIH (NIH Lam). The control was SBs cultured in suspension overnight in the presence of NIC (SBs NIC).

Figure 52:
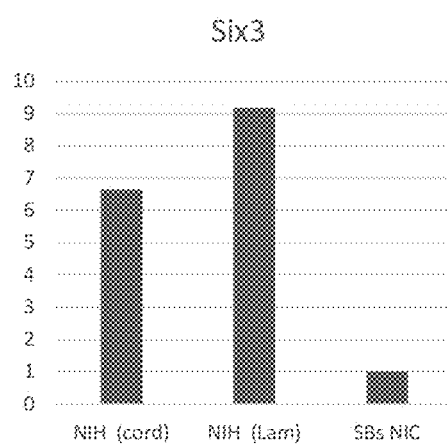

FIG. 52 is a graph illustrating the expression of the marker, Six3, by SBs that were derived from hESCs cultured on gelatin in NUTRISTEM® hPSC XF*Xeno-free medium conditioned by Cord-feeders and that were cultured in suspension in NIH (NIH cord) compared to expression by SBs derived from hESCs cultured on laminin 521 in NUTRISTEM® hPSC XF*Xeno-free medium which were cultured in suspension in NIH (NIH Lam). The control was SBs cultured in suspension overnight in the presence of NIC (SBs NIC).

Figure 53:
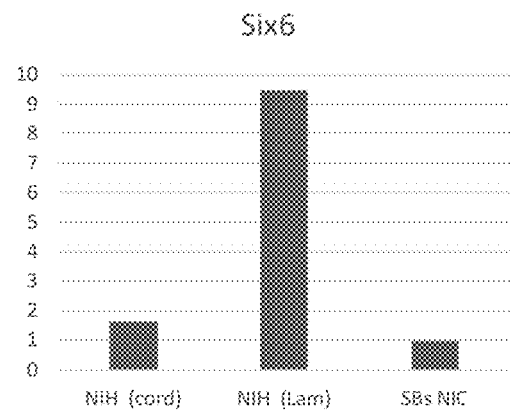

FIG. 53 is a graph illustrating the expression of the marker, Six6, by SBs that were derived from hESCs cultured on gelatin in NUTRISTEM® hPSC XF*Xeno-free medium conditioned by Cord-feeders and that were cultured in suspension in NIH (NIH cord) compared to expression by SBs derived from hESCs cultured on laminin 521 in NUTRISTEM® hPSC XF*Xeno-free medium which were cultured in suspension in NIH (NIH Lam). The control was SBs cultured in suspension overnight in the presence of NIC (SBs NIC).

FIG. 54 is a graph illustrating the expression of the marker, Chx10, by SBs that were derived from hESCs cultured on gelatin in NUTRISTEM® hPSC XF*Xeno-free medium conditioned by Cord-feeders and that were cultured in suspension in NIH (NIH cord) compared to expression by SBs derived from hESCs cultured on laminin 521 in NUTRISTEM® hPSC XF*Xeno-free medium which were cultured in suspension in NIH (NIH Lam). The control was SBs cultured in suspension overnight in the presence of NIC (SBs NIC).

FIG. 55 is a graph illustrating the expression of the marker, Rx, by SBs that were derived from hESCs cultured on gelatin in NUTRISTEM® hPSC XF*Xeno-free medium conditioned by Cord-feeders and that were cultured in suspension in NIH (NIH cord) compared to expression by SBs derived from hESCs cultured on laminin 521 in NUTRISTEM® hPSC XF*Xeno-free medium which were cultured in suspension in NIH (NIH Lam). The control was SBs cultured in suspension overnight in the presence of NIC (SBs NIC).

FIG. 56 is a graph illustrating the expression of the marker, Pax6, by SBs that were derived from hESCs cultured on gelatin in NUTRISTEM® hPSC XF*Xeno-free medium conditioned by Cord-feeders and that were cultured in suspension in NIH (NIH cord) compared to expression by SBs derived from hESCs cultured on laminin 521 in NUTRISTEM® hPSC XF*Xeno-free medium which were cultured in suspension in NIH (NIH Lam). The control was SBs cultured in suspension overnight in the presence of NIC (SBs NIC).

Figure 57:
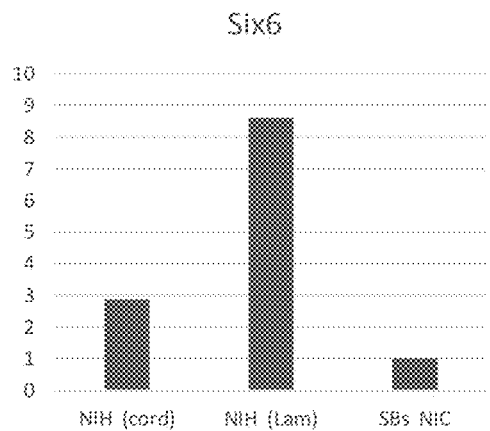

FIG. 57 is a graph illustrating the expression of the marker, Six6, by SBs that were derived from hESCs cultured on gelatin in NUTRISTEM® hPSC XF*Xeno-free medium conditioned by Cord-feeders and that were cultured in suspension in NIH (NIH cord) compared to expression by SBs derived from hESCs cultured on laminin 521 in NUTRISTEM® hPSC XF*Xeno-free medium which were cultured in suspension in NIH (NIH Lam). The control was SBs cultured in suspension overnight in the presence of NIC (SBs NIC).

Figure 58:
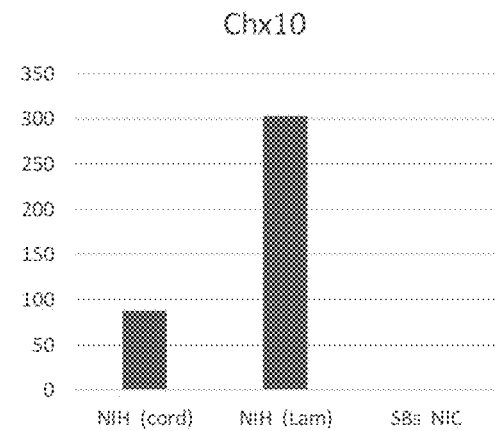

FIG. 58 is a graph illustrating the expression of the marker, Chx10, by SBs that were derived from hESCs cultured on gelatin in NUTRISTEM® hPSC XF*Xeno-free medium conditioned by Cord-feeders and that were cultured in suspension in NIH (NIH cord) compared to expression by SBs derived from hESCs cultured on laminin 521 in NUTRISTEM® hPSC XF*Xeno-free medium which were cultured in suspension in NIH (NIH Lam). The control was SBs cultured in suspension overnight in the presence of NIC (SBs NIC).

Figures 59A, 59B:
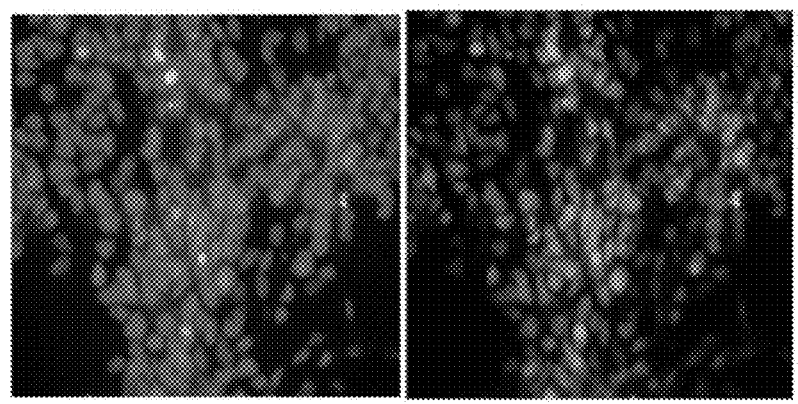

FIG. 59A is an image of hESC-derived photoreceptor progenitor cells stained in vitro with anti-RAX antibodies (red) and with DAPI nuclear counterstaining (blue).

FIG. 59B is an image of hESC-derived photoreceptor progenitor cells stained in vitro with anti-RAX antibodies (red) and GFP expression by the cells (green).

FIG. 60A is an image of hESC-derived photoreceptor progenitor cells stained in vitro with anti-Chx10 antibodies (red) and DAPI nuclear counterstaining (blue).

FIG. 60B is an image of hESC-derived photoreceptor progenitor cells stained in vitro with anti-Chx10 antibodies (red) and GFP expression by the cells (green).

FIG. 61A is an image of hESC-derived photoreceptor progenitor cells stained in vitro with anti-Crx (red) with DAPI nuclear counterstaining (blue).

FIG. 61B is an image of hESC-derived photoreceptor progenitor cells stained in vitro with anti-Crx antibodies (red) and GFP expression by the cells (green).

Figures 62A, 62B:
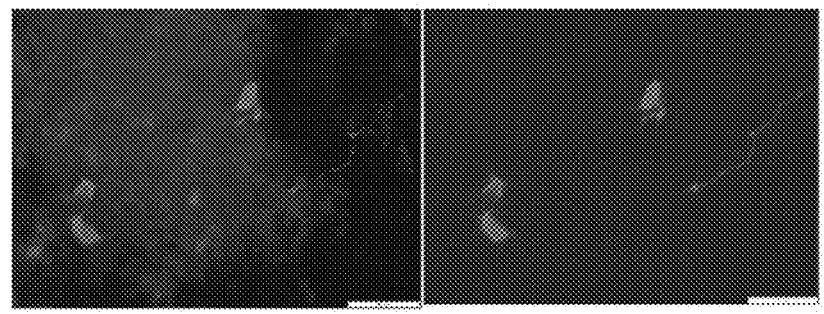
Figures 62C, 62D:
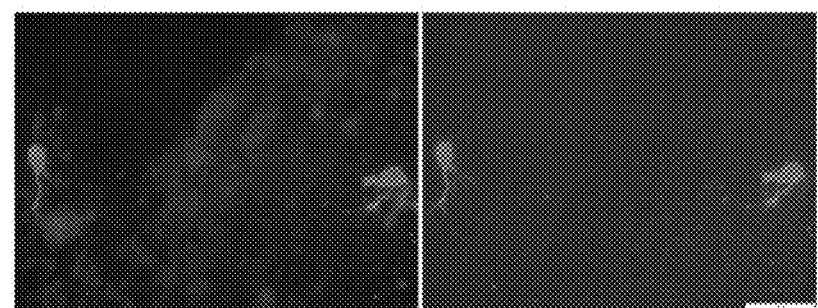

FIG. 62A and FIG. 62C are images of hESC-derived photoreceptor progenitor cells stained in vitro with anti-Recoverin (red) with DAPI nuclear counterstaining (blue).

FIG. 62B and FIG. 62D are images of hESC-derived photoreceptor progenitor cells stained in vitro with anti-Recoverin (red).

Figures 63A, 63B:
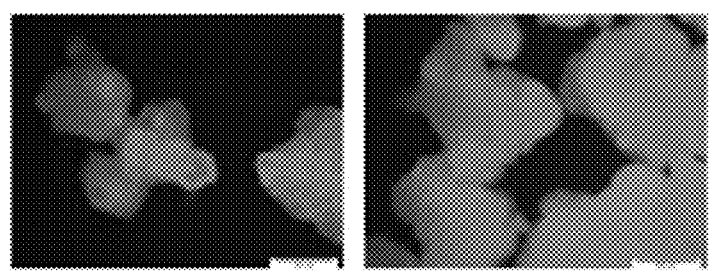

FIG. 63A and FIG. 63B are images of hESC-derived SBs that were engineered to express GFP.

Figure 64:
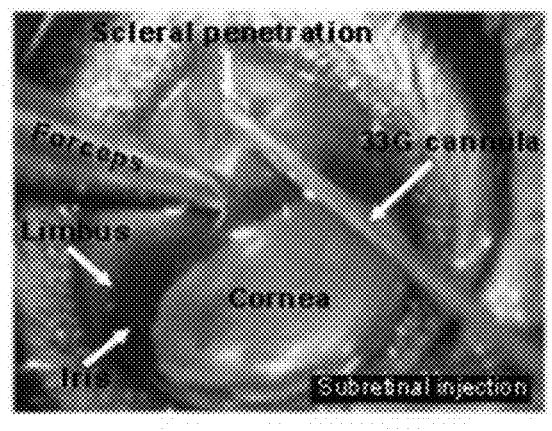

FIG. 64 is an image of the subretinal transplantation procedure, according to certain embodiments.

Figure 65:
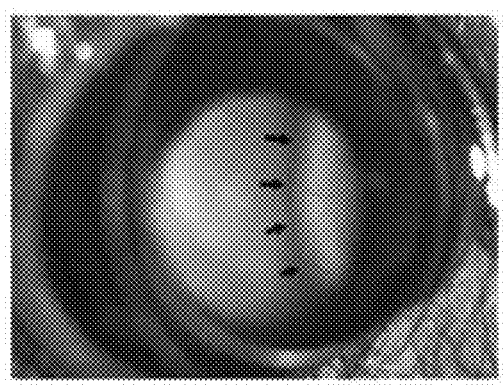

FIG. 65 is an image of a subretinal bleb formed after the transplantation procedure, (border of bleb marked by black arrows) according to certain embodiments.

Figure 66:
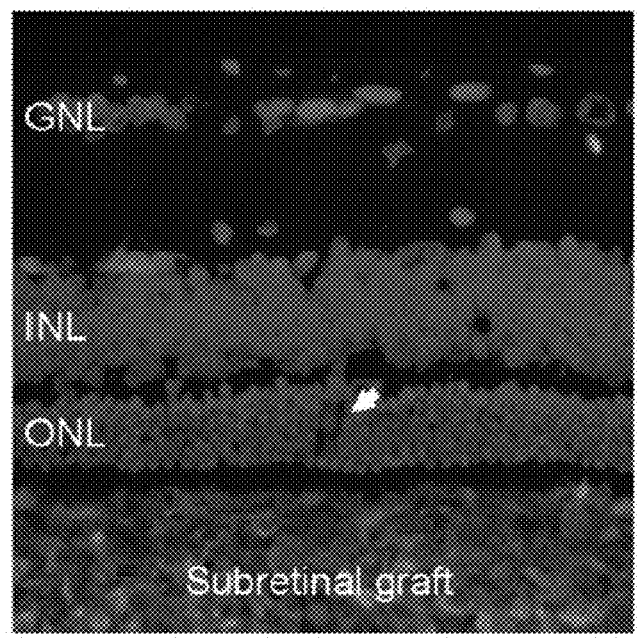

FIG. 66 is an image of hESC-derived photoreceptor progenitor cells 4 weeks post transplantation of the cells into the subretinal space. Cells were engineered to express GFP and were stained with anti-GFP antibodies (green). Engraftment of the transplanted cells can be seen in the subretinal space with migration into the different retinal layers. Sporadic GFP-positive cells are incorporated in the Outer Nuclear (photoreceptors) Layer (ONL, arrow). Nuclei were counterstained with DAPI (blue).

Figure 67:
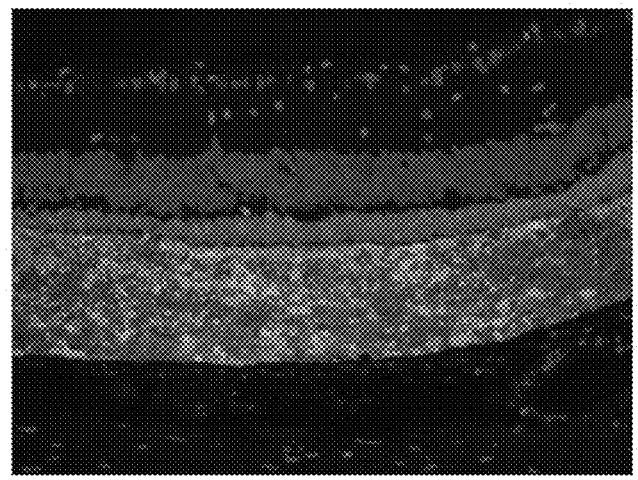

FIG. 67 is an image of hESC-derived photoreceptor progenitor cells 7 weeks post transplantation of the cells into the subretinal space. Cells were engineered to express GFP and were stained with anti-GFP antibodies (green). The cells were also stained for rhodopsin, the rod-photoreceptor-specific marker (red). Host rod photoreceptors also express rhodopsin, but not GFP (green). Nuclei were counterstained with DAPI (blue).

Figure 68:
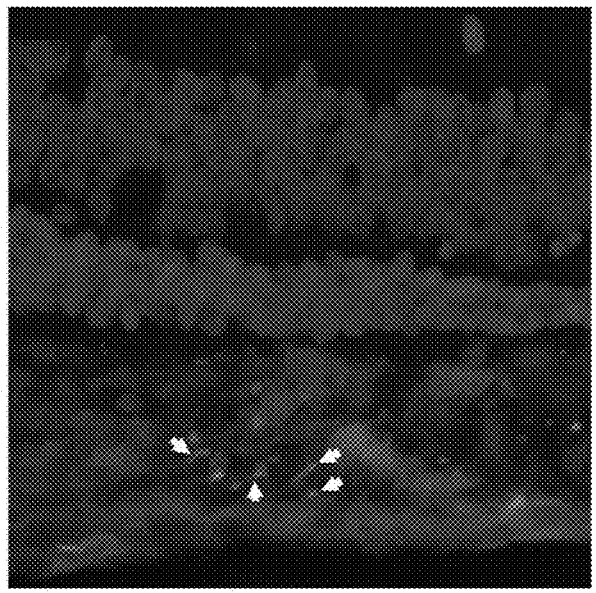

FIG. 68 is an image of transplanted cells (green) in a subretinal graft expressing the cone-photoreceptor-specific marker red/green opsin (red, arrows), at 7 weeks post-transplantation. Nuclei were counterstained with DAPI (blue).

Figure 69:
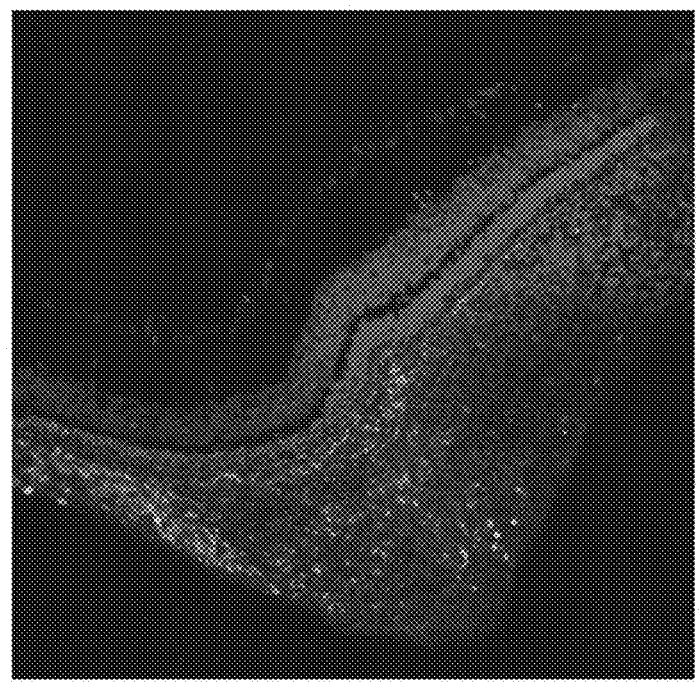

FIG. 69 is an image of GFP-expressing hESC-derived photoreceptor progenitors 4-6 weeks post subretinal transplantation. The photoreceptor progenitors identified using immunohistochemical co-staining with anti-GFP (green) and anti-rhodopsin (red), Nuclei were counterstained with DAPI (blue). The hESC were treated in vitro with NIC+IWR1e+HSA prior transplantation to induce differentiation into photoreceptor progenitors. Magnification 20×.

Figure 70:
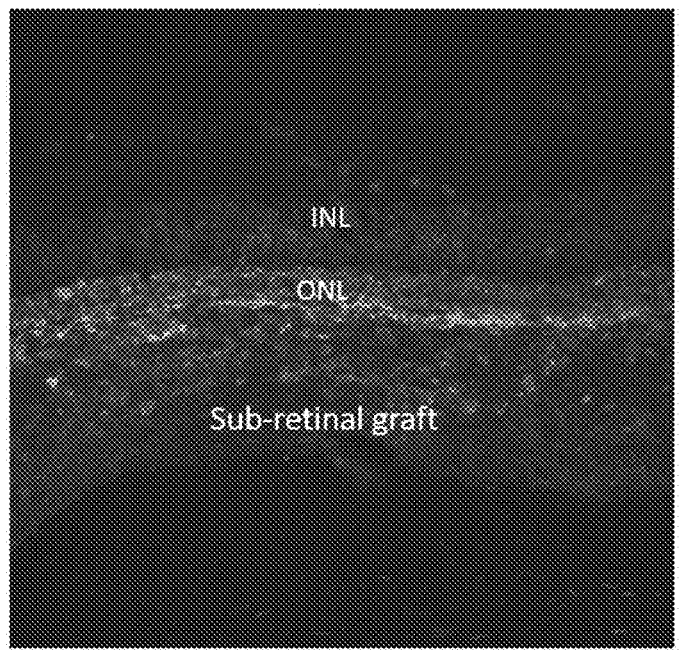

FIG. 70 is an image of GFP-expressing hESC-derived photoreceptor progenitors 4-6 weeks post subretinal transplantation. The photoreceptor progenitors identified using immunohistochemical co-staining with anti-GFP (green) and anti-rhodopsin (red). Nuclei were counterstained with DAPI (blue). The hESC were treated in vitro with NIC+IWR1e+HSA prior transplantation to induce differentiation into photoreceptor progenitors. Magnification 40×.

Figure 71:
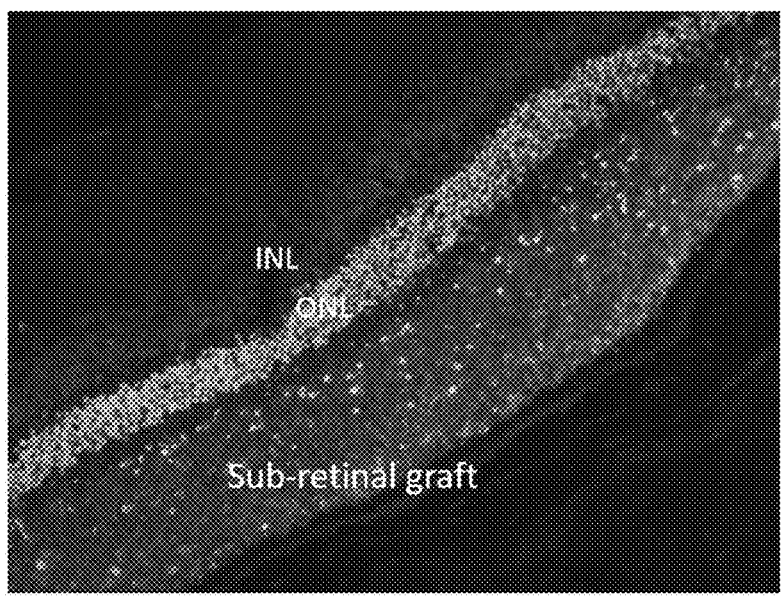

FIG. 71 is an image of GFP-expressing hESC-derived photoreceptor progenitors 4-6 weeks post subretinal transplantation. The photoreceptor progenitors identified using immunohistochemical co-staining with anti-GFP (green) and antibodies against red/green opsin (red). Nuclei were counterstained with DAPI (blue). The hESC were treated in vitro with NIC+IWR1e+HSA prior transplantation to induce differentiation into photoreceptor progenitors. Magnification 40×.

DETAILED DESCRIPTION

The present invention, in some embodiments thereof, relates to methods of preparing photoreceptor cells from pluripotent stem cells.

Before explaining at least one embodiment, it is to be understood that the disclosure is not necessarily limited in its application to the details set forth in the following description or exemplified by the Examples. The embodiments are capable of being practiced or carried out in various ways.

Human embryonic stem cells have been proposed as a cellular source for the generation of retinal cells including retinal pigment epithelium (RPE) cells and photoreceptor cells.

Whilst reducing embodiments of the invention to practice, the present inventors uncovered that nicotinamide alone or in specific combinations thereof with IWRe, bFGF, IGF and/or CHIR are sufficient to generate photoreceptor cells from human pluripotent stem cells, as evidenced by the expression of markers of photoreceptor cells (e.g., RT-PCR). It was demonstrated that transplanted photoreceptor cells were viable in the subretinal space of a rodent model even 7 weeks post-transplantation. The graft expresses the cone-photoreceptor-specific markers.

The term "photoreceptor cells" (abbreviated as photoreceptors) as used herein refers to biological cells that are capable of phototransduction. The term also refers to photoreceptor cell precursors/progenitors that express moderate levels of CRX and NRL (see for example FIG. 7, FIG. 8, FIG. 13, and FIG. 14) yet are able to differentiate to photoreceptors upon transplantation to the subretinal space. The photoreceptors of this aspect of the present invention may be rods and/or cones. Preferably, upon transplantation within an eye, they exhibit functional activities similar to those of native photoreceptors.

According to certain embodiments, the photoreceptor cells express at least one, two, three, or four markers of photoreceptor cells. Such markers include, but are not limited to CHX10/VSX2 (visual system homeobox 2), rhodopsin, CRX, Arrestin, Opsin, Recoverin and NRL (neural retina-specific leucine zipper protein).

According to still other embodiments, the photoreceptor cells are capable of treating diseases such as macular degeneration.

"Retinal pigment epithelium cells", "RPE cells", "RPEs", which may be used interchangeably as the context allows, refers to cells of a cell type functionally similar to that of native RPE cells which form the pigment epithelium cell layer of the retina (e.g., upon transplantation within an eye, they exhibit functional activities similar to those of native RPE cells).

According to one embodiment, the RPE cell expresses at least one, two, three, four or five markers of mature RPE cells. Such markers include, but are not limited to CRALBP, RPE65, PEDF, PMEL17, Bestrophin, ZO-1 and tyrosinase. Optionally, the RPE cells may also express a marker of an RPE progenitor—e.g., MITF. In another embodiment, the RPE cells express PAX-6. In another embodiment, the RPE cells express at least one marker of a retinal progenitor cell including, but not limited to Rx, OTX2 or SIX3. Optionally, the RPE cells express either SIX6 and/or LHX2.

As used herein, the phrase "markers of mature RPE cells" refers to antigens (e.g., proteins) that are elevated (e.g., at least 2 fold, at least 5 fold, at least 10 fold) in mature RPE cells with respect to non RPE cells or immature RPE cells.

As used herein, the phrase "markers of RPE progenitor cells" refers to antigens (e.g., proteins) that are elevated (e.g., at least 2 fold, at least 5 fold, at least 10 fold) in RPE progenitor cells with respect to non RPE cells.

According to another embodiment, the RPE cells have a morphology similar to that of native RPE cells which form the pigment epithelium cell layer of the retina i.e. pigmented and having a characteristic polygonal shape.

According to still another embodiment, the RPE cells are capable of treating diseases such as macular degeneration.

According to still another embodiment, the RPE cells fulfill at least 1, 2, 3, 4 or all of the requirements listed herein above.

As used herein, the phrase "stem cells" refers to cells which are capable of remaining in an undifferentiated state (e.g., pluripotent or multipotent stem cells) for extended periods of time in culture until induced to differentiate into other cell types having a particular, specialized function (e.g., fully differentiated cells). Preferably, the phrase "stem cells" encompasses embryonic stem cells (ESCs), induced pluripotent stem cells (iPSCs), adult stem cells, mesenchymal stem cells and hematopoietic stem cells.

According to a particular embodiment, the photoreceptor cells are generated from pluripotent stem cells (e.g., ESCs or iPSCs).

Induced pluripotent stem cells (iPSCs) can be generated from somatic cells by genetic manipulation of somatic cells, e.g., by retroviral transduction of somatic cells such as fibroblasts, hepatocytes, gastric epithelial cells with transcription factors such as Oct-3/4, Sox2, c-Myc, and KLF4 [Yamanaka S, Cell Stem Cell. 2007, 1(1):39-49; Aoi T, et al., Generation of Pluripotent Stem Cells from Adult Mouse Liver and Stomach Cells. Science. 2008 Feb. 14. (Epub ahead of print); IH Park, Zhao R, West J A, et al., Reprogramming of human somatic cells to pluripotency with defined factors. Nature 2008; 451:141-146; K Takahashi, Tanabe K, Ohnuki M, et al., Induction of pluripotent stem cells from adult human fibroblasts by defined factors. Cell 2007; 131: 861-872]. Other embryonic-like stem cells can be generated by nuclear transfer to oocytes, fusion with embryonic stem cells or nuclear transfer into zygotes if the recipient cells are arrested in mitosis. In addition, iPSCs may be generated using non-integrating methods e.g., using small molecules or RNA.

The phrase "embryonic stem cells" refers to embryonic cells which are capable of differentiating into cells of all three embryonic germ layers (i.e., endoderm, ectoderm and mesoderm), or remaining in an undifferentiated state. The phrase "embryonic stem cells" may comprise cells which are obtained from the embryonic tissue formed after gestation (e.g., blastocyst) before implantation of the embryo (i.e., a pre-implantation blastocyst), extended blastocyst cells (EBCs) which are obtained from a post-implantation/pre-gastrulation stage blastocyst (see WO2006/040763) and embryonic germ (EG) cells which are obtained from the genital tissue of a fetus any time during gestation, preferably before 10 weeks of gestation. The embryonic stem cells of some embodiments of the invention can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells, the zona pellucida is removed from the blastocyst and the inner cell mass (ICM) is isolated by a procedure in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells see Reubinoff et al., Nat Biotechnol 2000, May: 18(5): 559; Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; and Gardner et al., [Fertil. Steril. 69: 84, 1998].

It will be appreciated that commercially available stem cells can also be used according to some embodiments of the invention. Human ES cells can be purchased from the NIH human embryonic stem cells registry [www(dot)grants(dot)nih(dot)gov/stem_cells/registry/current(dot)htm] or from other hESC registries. Non-limiting examples of commercially available embryonic stem cell lines are HAD-C102, HAD-C100, HAD-C106, HAD-C105, HAD-C104, HADC-C103, HAD-C107, ESI, BG01, BG02, BG03, BG04, CY12, CY30, CY92, CYTO, TE03, TE32, CHB-4, CHB-5, CHB-6, CHB-8, CHB-9, CHB-10, CHB-11, CHB-12, HUES 1, HUES 2, HUES 3, HUES 4, HUES 5, HUES 6, HUES 7, HUES 8, HUES 9, HUES 10, HUES 11, HUES 12, HUES 13, HUES 14, HUES 15, HUES 16, HUES 17, HUES 18, HUES 19, HUES 20, HUES 21, HUES 22, HUES 23, HUES 24, HUES 25, HUES 26, HUES 27, HUES 28, CyT49, RUES3, WA01, UCSF4, NYUES1, NYUES2, NYUES3, NYUES4, NYUES5, NYUES6, NYUES7, UCLA 1, UCLA 2, UCLA 3, WA077 (H7), WA09 (H9), WA13 (H13), WA14 (H14), HUES 62, HUES 63, HUES 64, CT1, CT2, CT3, CT4, MA135, Eneavour-2, WIBR1, WIBR2, WIBR3, WIBR4, WIBR5, WIBR6, HUES 45, Shef 3, Shef 6, BJN-hem19, BJNhem20, SA001, SA001.

According to a specific embodiment, the embryonic stem cell line is HAD-C102 or ESI.

In addition, ES cells can be obtained from other species as well, including mouse (Mills and Bradley, 2001), golden hamster [Doetschman et al., 1988, Dev Biol. 127: 224-7], rat [Iannaccone et al., 1994, Dev Biol. 163: 288-92] rabbit [Giles et al., 1993, Mol Reprod Dev. 36: 130-8; Graves & Moreadith, 1993, Mol Reprod Dev. 1993, 36: 424-33], several domestic animal species [Notarianni et al., 1991, J Reprod Fertil Suppl. 43: 255-60; Wheeler 1994, Reprod Fertil Dev. 6: 563-8; Mitalipova et al., 2001, Cloning. 3: 59-67] and non-human primate species (Rhesus monkey and marmoset) [Thomson et al., 1995, Proc Natl Acad Sci USA. 92: 7844-8; Thomson et al., 1996, Biol Reprod. 55: 254-9].

Extended blastocyst cells (EBCs) can be obtained from a blastocyst of at least nine days post fertilization at a stage prior to gastrulation. Prior to culturing the blastocyst, the zona pellucida is digested [for example by Tyrode's acidic solution (Sigma Aldrich, St Louis, MO, USA)] so as to expose the inner cell mass. The blastocysts are then cultured as whole embryos for at least nine and no more than fourteen days post fertilization (i.e., prior to the gastrulation event) in vitro using standard embryonic stem cell culturing methods.

Another method for preparing ES cells is described in Chung et al., Cell Stem Cell, Volume 2, Issue 2, 113-117, 7 Feb. 2008. This method comprises removing a single cell from an embryo during an in vitro fertilization process. The embryo is not destroyed in this process.

EG cells are prepared from the primordial germ cells obtained from fetuses of about 8-11 weeks of gestation (in the case of a human fetus) using laboratory techniques known to anyone skilled in the arts. The genital ridges are dissociated and cut into small chunks which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparation human EG cells see Shamblott et al., [Proc. Natl. Acad. Sci. USA 95: 13726, 1998] and U.S. Pat. No. 6,090,622.

The pluripotent stem cells may be in the naïve or primed pluripotent state.

The pluripotent stem cells may be obtained from totipotent stem cells derived from the blastomere state.

Yet another method for preparing ES cells is by parthenogenesis. The embryo is also not destroyed in the process.

Currently practiced ES culturing methods are mainly based on the use of feeder cell layers which secrete factors needed for stem cell proliferation, while at the same time, inhibit their differentiation. The culturing is typically effected on a solid surface—e.g., a surface coated with gelatin or vimentin. Exemplary feeder layers include Human embryonic fibroblasts, adult fallopian epithelial cells, primary mouse embryonic fibroblasts (PMEF), mouse embryonic fibroblasts (MEF), murine fetal fibroblasts (MFF), human embryonic fibroblast (HEF), human fibroblasts obtained from the differentiation of human embryonic stem cells, human fetal muscle cells (HFM), human fetal skin cells (HFS), human adult skin cells, human foreskin fibroblasts (HFF), human umbilical cord fibroblasts, human cells obtained from the umbilical cord or placenta, and human marrow stromal cells (hMSCs). Growth factors may be added to the medium to maintain the ESCs in an undifferentiated state. Such growth factors include bFGF and/or TGFβ. In another embodiment, agents may be added to the medium to maintain the hESCs in a naïve undifferentiated state—see for example Kalkan et al., 2014, Phil. Trans. R. Soc. B, 369: 20130540.

Human cord fibroblasts may be expanded in Dulbecco's Modified Eagle's Medium (e.g., DMEM, SH30081.01, Hyclone) supplemented with human serum (e.g., 20%) and glutamine Preferably the human cord cells are irradiated. This may be effected using methods known in the art (e.g., Gamma cell, 220 Exel, MDS Nordion 3,500 rads). Once sufficient cells are obtained they may be frozen (e.g., cryopreserved). For expansion of ESCs, the human cord fibroblasts are typically seeded on a solid surface (e.g., T75 or T175 flasks) optionally coated with an adherent substrate such as gelatin (e.g., recombinant human gelatin (RhG100-001, Fibrogen) at a concentration of 25-40,000 cells/cm$^2$ in DMEM (e.g., SH30081.01, Hyclone) supplemented with about 20% human serum (and glutamine) hESCs are typically plated on top of the feeder cells 1-4 days later in a supportive medium (e.g., NUTRISTEM® with human serum albumin). Additional factors may be added to the medium to prevent differentiation of the ESCs such as bFGF and TGF-β. Once a sufficient amount of hESCs are obtained, the cells may be mechanically disrupted (e.g., by using a sterile tip or a disposable sterile stem cell tool; 14602 Swemed). Alternatively, the cells may be removed by enzymatic treatment (e.g., collagenase A, or TRYPLE SELECT™) or chemical treatment (e.g., EDTA). This process may be repeated several times to reach the necessary amount of hESC. According to a particular embodiment, following the first round of expansion, the hESCs are removed using TRYPLE SELECT™ and following the second round of expansion, the hESCs are removed using collagenase A.

Human embryonic fibroblasts or adult fallopian epithelial cells as feeder cell layers—Human ES cells can be grown and maintained using human embryonic fibroblasts or adult fallopian epithelial cells. When grown on these human feeder cells the human ES cells exhibit normal karyotypes, present alkaline phosphatase activity, express Oct-4 and other embryonic cell surface markers including SSEA-3, SSEA-4, TRA-1-60, and GC™-2, form teratomas in vivo, and retain all key morphological characteristics [Richards M, Fong C Y, Chan W K, Wong P C, Bongso A. (2002). Human feeders support prolonged undifferentiated growth of human inner cell masses and embryonic stem cells. Nat. Biotechnol. 20: 933-6].

Foreskin feeder layers—Human ES cells can be cultured on human foreskin feeder layer as disclosed in U.S. patent application Ser. No. 10/368,045. Foreskin derived feeder cell layers consist of a complete animal-free environment suitable for culturing human ES cells. In addition, foreskin cells can be maintained in culture for as long as 42 passages since their derivation, providing the ES cells with a relatively constant environment. Under these conditions the human ES cells were found to be functionally indistinct from cells grown with alternate protocols (e.g., MEF). Following differentiation, ES cells expressed genes associated with all three embryonal germ layers, in vitro, and formed teratomas in vivo, consisting of tissue arising from all three germ layers.

Feeder cell free systems have also been used in ES cell culturing, such systems utilize matrices supplemented with serum replacement, cytokines and growth factors (including IL6 and soluble IL6 receptor chimera) as a replacement for the feeder cell layer. Stem cells can be grown on a solid surface such as an extracellular matrix (e.g., MATRIGEL™ or laminin) in the presence of culture medium—for example the Lonza L7™ system, MTESR™, STEMPRO™, XFKSR, ESSENTIAL 8™, NUTRISTEM®). Unlike feeder-based cultures which require the simultaneous growth of feeder cells and stem cells and which may result in mixed cell populations, stem cells grown on feeder-free systems are easily separated from the surface.

According to a specific embodiment, the he ESCs may be expanded on feeders prior to the differentiation step.

The human pluripotent stem cells may be cultured in conditioned medium prior to the first stage of directed differentiation. The feeder cell-conditioned medium is isolated from (or collected from) the feeder cells which are used to generate said feeder cell-conditioned medium. Thus, the human pluripotent stem cells are preferably cultured in a different container to the container used for generating the cell-conditioned medium. Although, trace amounts of feeder cells may be comprised in the conditioned medium, preferably, this culturing step is typically carried out in the absence of feeder cells. Culturing the human pluripotent stem cells is typically effected for at least one day, more preferably at least two days e.g. two days, three days, four days, five days, six days or seven days. Preferably, the culturing in conditioned medium is not carried out for more than 21 days, e.g. not more than 14 days. According to a particular embodiment, the culturing is effected on a dish or a flask (e.g., T75 flask or T175 flask). The solid surface may be coated with a non-adherent substrate such as fibronectin, laminin, polyD-lysine or gelatin. After a suitable length of time, human pluripotent stem cells colonies may be removed from the solid surface using a suitable agent—for example using collagenase A, dispase, TrypLE select, or EDTA.

Conditioned Medium

Conditioned medium is the growth medium of a monolayer cell culture (i.e., feeder cells) present following a certain culturing period. The conditioned medium includes growth factors and cytokines secreted by the monolayer cells in the culture.

The conditioned medium of the present invention can be collected from a variety of human cells forming monolayers in culture. Examples include human foreskin conditioned medium, human embryonic fibroblasts conditioned medium, human fallopian epithelial cells conditioned medium, and human cord fibroblast conditioned medium.

Particularly suitable conditioned medium are those derived from human cells, such as human cord fibroblast-conditioned medium which is produced by culturing human cord fibroblast cells in a growth medium under conditions suitable for producing the conditioned medium.

According to a specific embodiment, the feeder cells are mitotically inactivated by irradiation. Other methods of inactivation may be used such as Mitomycin treatment.

Such a growth medium can be any medium suitable for culturing feeder cells. The growth medium can be supplemented with nutritional factors, such as amino acids, (e.g., L-glutamine), anti-oxidants (e.g., beta-mercaptoethanol) and growth factors, which benefit stem cell growth in an undifferentiated state. Serum and serum replacements are added at effective concentration ranges as described elsewhere (U.S. patent application Ser. No. 10/368,045).

Feeder cells are cultured in the growth medium for sufficient time to allow adequate accumulation of secreted factors to support stem cell proliferation in an undifferentiated state. Typically, the medium is conditioned by culturing for 4-48 hours at 37° C. However, the culturing period can be scaled by assessing the effect of the conditioned medium on stem cell growth and differentiation.

According to a particular embodiment the conditioned medium is prepared by seeding irradiated human cord cells in a medium (e.g., DMEM) in the presence of human serum for about 5-24 hours. Longer culture periods up to about 7 days may also be effective. The cells are then cultured in a medium (e.g., NUTRISTEM®) in the absence of human serum for another 24 hours. The second medium may comprise human serum albumin. Furthermore, the second medium may comprise growth factors such as basic FGF and factors from the TGFβ superfamily to prevent differentiation. According to a particular embodiment, the culture dishes on which the conditioned medium is prepared are not coated with gelatin. According to another embodiment, the culture media which are used to prepare the conditioned medium do not comprise fibroblast growth factor (FGF) or TGFβ superfamily factors.

Selection of culture apparatus for conditioning the medium is based on the scale and purpose of the conditioned medium. Large-scale production preferably involves the use of dedicated devices. According to a particular embodiment, the conditioned medium is prepared in flasks. Continuous cell culture systems are reviewed in Furey (2000) Genetic Eng. News 20:10.

Following accumulation of adequate factors in the medium, growth medium (i.e., conditioned medium) is separated from the feeder cells and collected. It will be appreciated that the feeder cells can be used repeatedly to condition further batches of medium over additional culture periods, provided that the cells retain their ability to condition the medium.

Preferably, the conditioned medium is sterilized (e.g., filtration using a 20 µM filter) prior to use. The conditioned medium of some embodiments of the invention may be applied directly on pluripotent stem cells or extracted to concentrate the effective factor such as by salt filtration. For future use, conditioned medium is preferably stored frozen at −80° C.

It will be appreciated that the present invention contemplates additional steps prior to the feeder-free conditioned medium step which aid in the expansion of the pluripotent stem cells.

Thus, according to a particular embodiment, the ESCs are expanded on feeders prior to the feeder-free conditioned medium step. Exemplary feeder layer based cultured contemplated by the present invention are described herein below. The expansion is typically effected for at least two days, three days, four days, five days, six days or seven days. The expansion is effected for at least 1 passage, or at least 2, at least 3, at least 4, at least 5, at least 6, at least 7, at least 8, at least 9 or at least 10 passages.

Following expansion, the pluripotent stem cells (e.g., ESCs) can be subjected to directed differentiation using a differentiating agent.

In additional embodiments, the ESC's may be cultured or expanded in feeder-free systems. Feeder-free systems can provide a more efficient and controlled culturing system. For example, ESCs may be cultured on laminin. In another example, ESCs may be cultured or expanded on laminin 521 in NUTRISTEM® hPSC XF*Xeno-free medium to generate cell aggregates or spheroid bodies (SBs). In some embodiments, the SBs can be treated with a differentiation agent, such as NIC.

As mentioned, photoreceptor cells may be produced by:
(a) culturing a population of human pluripotent stem cells in a medium comprising at least 0.5 mM nicotinamide, wherein said culture does not comprise any member of the TGFβ superfamily at a concentration which allows differentiation into said photoreceptor cells; and
(b) isolating said photoreceptor cells from retinal pigmented epithelial (RPE) cells, thereby generating the photoreceptors.

Alternatively,
(a) culturing a population of human pluripotent stem cells in a medium comprising at least 0.5 mM nicotinamide to obtain differentiating cells; and
(b) culturing said differentiating cells in a medium which comprises at least one agent selected from the group consisting of a Wnt inhibitor, bFGF, IGF and a GSK3 inhibitor to generate photoreceptor cells; and optionally (c) isolating said photoreceptor cells, thereby generating the photoreceptor cells.

Thus, the protocol may involve culturing the pluripotent stem cells in the presence of nicotinamide such that photoreceptor cells are formed; or followed by a further stage (distinct) of differentiation which involves the addition of factors, as mentioned hereinabove typically absent from the first step of differentiation with nicotinamide.

According to a particular embodiment, nicotinamide (NA, NIC) is provided at a concentration of at least 0.5 µM—e.g. between 0.5-100 µM, 0.05-50 µM, 5-50 µM, 5-20 µM, e.g. 10 µM.

According to a specific embodiment, NA is provided at about the same concentration in the first differentiation step and in the second differentiation step where multiple steps of differentiation are involved (i.e., at least 2, as mentioned above) involving the addition of factors e.g., a Wnt inhibitor, bFGF, HSA, IGF and/or GSK3 inhibitor.

Exemplary embodiments may include the following combinations at the second step of differentiation.
(i) nicotinamide and Wnt inhibitor;
(i) nicotinamide and bFGF;
(ii) nicotinamide and IGF;
(iii) nicotinamide, IGF and a GSK3 inhibitor; or
(v) nicotinamide, bFGF and Wnt inhibitor
(vi) nicotinamide, Wnt inhibitor and HSA
(vii) nicotinamide, bFGF, and HSA
(viii) nicotinamide, bFGF, Wnt inhibitor and HSA
(ix) nicotinamide, and HSA As used herein "Wnt inhibitor" refers to a molecule capable of suppressing signal transduction mediated by Wnt. Wnt signal inhibitors include, but are not limited to, for example, IWR-1-endo(4-[(3aR,4S,7R,7aS)-1,3,3a,4,7,7a-hexahydro-1,3-dioxo-4,7-metha-no-2H-isoindol-2-yl]-N-8-quinolinyl-benzamide), IWP-2, XAV939, Dkk1, Cerberus protein, Wnt receptor inhibitors, soluble Wnt receptors, Wnt antibodies, casein kinase inhibitors, and dominant negative Wnt protein; in particular, IWR-1-endo preferably.

According to a specific embodiment, the Wnt inhibitor is provided at a concentration of between about 0.1 µM-20 µM. Exemplary ranges include, but are not limited to 0.1 µM-15 µM, 0.1 µM-10 µM, 0.5 µM-20 µM, 1 µM-20 µM, 1 µM-10 µM, 1 µM-5 µM.

As used herein "IGF1" or "Insulin-like growth factor 1 (IGF-1)", also called somatomedin C, refers to a protein that in humans is encoded by the IGF1 gene. IGF-1 has also been referred to as a "sulfation factor". IGF1 is available from numerous vendors such as from R&D Systems Inc., Catalog Number 291-G1).

As used herein, "GSK3 inhibitor" refers to GSK3b inhibitor i.e., the glycogen synthase kinase 3 beta protein set forth by GenBank Accession Nos. NP_002084.2 (SEQ ID NO: 121) and/or NP_001139628.1 (SEQ ID NO: 122) having the WNT signaling regulatory activity via its kinase activity.

As used herein, the term "GSK3b inhibitor" refers to a molecule capable of inhibiting the activity of GSK3b as determined by specifically inhibiting levels of phosphorylated GSK3b (out of total GSK3b present in a cell).

Non-limiting examples of GSK3b inhibitors include CHIR99021 (CHIR, PeproTech Inc., Rocky Hill, NJ)), BIO (AXONMEDCHEM—Axon 1693), and Kenpaullone (TOCRIS—cat no. 1398).

According to some embodiments, CHIR99021 is provided at a concentration range of between about 0.1 µM-50 µM, 0.1 µM-20 µM-µM, e.g., from about 0.2 µM to about 20 µM, e.g., between about 0.5-20 µM, e.g., between about 1-10 µM.

The phrases "basic fibroblast growth factor (bFGF)" or "FGF2" which are interchangeably used herein refer to a polypeptide of the fibroblast growth factor (FGF) family, which bind heparin and possess broad mitogenic and angiogenic activities. The mRNA for the BFGF gene contains multiple polyadenylation sites, and is alternatively translated from non-AUG (CUG) and AUG initiation codons, resulting in five different isoforms with distinct properties. The CUG-initiated isoforms are localized in the nucleus and are responsible for the intracrine effect, whereas, the AUG-initiated form is mostly cytosolic and is responsible for the paracrine and autocrine effects of this FGF. According to some embodiments of the invention, the bFGF used by the medium of some embodiments of the invention is provided in GenBank Accession No. NP_001997. bFGF can be obtained from various manufacturers such as Peprotech, RnD systems (Catalog Number:100-18B).

According to some embodiments, bFGF is provided at a concentration range from about 1 nanogram per milliliter (ng/ml) to about 50 ng/ml, e.g., about 1-40 ng/ml, e.g., about 1-50 ng/ml, e.g., about 1-40 ng/ml, e.g., about 1-30 ng/ml, e.g., about 1-20 ng/ml, e.g., about 2-20 ng/ml, e.g., about 2-10 ng/ml, e.g., about 3-10 ng/ml, e.g., about 4-10 ng/ml, e.g., about 8 ng/ml.

According to a specific embodiment, the differentiation conditions described herein do not include a TGFbeta superfamily member (e.g., Activin A) at a concentration which allows differentiation of differentiating cells (e.g., after a first step of differentiation with NA alone at a concentration of at least 0.5 mM) towards photoreceptor cells.

According to a specific embodiment, the factor is a human factor.

Any of these factors can be naturally occurring (purified), recombinant or chemically synthesized.

NA, also known as "niacinamide", is the amide derivative form of Vitamin B3 (niacin) which is thought to preserve and improve beta cell function. NA has the chemical formula $C_6H_6N_2O$. NA is essential for growth and the conversion of foods to energy, and it has been used in arthritis treatment and diabetes treatment and prevention.

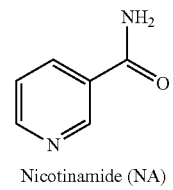

Nicotinamide (NA)

According to a particular embodiment, the nicotinamide is a nicotinamide derivative or a nicotinamide mimic. The term "derivative of nicotinamide (NA)" as used herein denotes a compound which is a chemically modified derivative of the natural NA. In one embodiment, the chemical modification may be a substitution of the pyridine ring of the basic NA structure (via the carbon or nitrogen member of the ring), via the nitrogen or the oxygen atoms of the amide moiety. When substituted, one or more hydrogen atoms may be replaced by a substituent and/or a substituent may be attached to a N atom to form a tetravalent positively charged nitrogen. Thus, the nicotinamide of the present invention includes a substituted or non-substituted nicotinamide. In another embodiment, the chemical modification may be a deletion or replacement of a single group, e.g., to form a thiobenzamide analog of NA, all of which being as appreciated by those versed in organic chemistry. The derivative in the context of the invention also includes the nucleoside derivative of NA (e.g., nicotinamide adenine). A variety of derivatives of NA are described, some also in connection with an inhibitory activity of the PDE4 enzyme (WO03/068233; WO02/060875; GB2327675A), or as VEGF-receptor tyrosine kinase inhibitors (WO01/55114). For example, the process of preparing 4-aryl-nicotinamide derivatives is disclosed in WO05/014549. Other exemplary nicotinamide derivatives are disclosed in WO01/55114 and EP2128244.

Nicotinamide mimics include modified forms of nicotinamide, and chemical analogs of nicotinamide which recapitulate the effects of nicotinamide in the differentiation and maturation of RPE cells from pluripotent cells. Exemplary nicotinamide mimics include benzoic acid, 3-aminobenzoic acid, and 6-aminonicotinamide. Another class of compounds that may act as nicotinamide mimics are inhibitors of poly(ADP-ribose) polymerase (PARP). Exemplary PARP inhibitors include 3-aminobenzamide, Iniparib (BSI 201), Olaparib (AZD-2281), Rucaparib (AG014699, PF-01367338), Veliparib (ABT-888), CEP 9722, MK 4827, and BMN-673.

When the process involves only NA without the addition of other factors (e.g., TGFbeta superfamily members) e.g., used in a single differentiation stage, culturing with NA is effected for at least 7-days e.g., up to 30 days.

In the sequential differentiation process i.e., at least two stages of differentiation culture, the differentiation is effected as follows:

a) culture of ESCs in a medium comprising nicotinamide (at least 0.5 mM). This step may be effected for a minimum of one day, two days, three days, 4 days, 5 days, 6 days, 1 week, 10 days, 2 weeks, three weeks, four weeks, five weeks or even 6 weeks. According to a specific embodiment, culturing with NA alone (without the addition of the indicated factors) is effected for 3-6 days.

b) culture of cells obtained from step a) in a medium comprising at least one agent (i.e., factor) selected from the group consisting of a Wnt inhibitor, bFGF, IGF1 and a GSK3 inhibitor and optionally together with the first differentiating agent (e.g., nicotinamide). This step may be effected for a minimum of one day, two days, three days, 4 days, 5 days, 6 days, 1 week, 10 days, 2 weeks, 17 days, three weeks, 30 days, four weeks, five weeks or even 6 weeks.

Preferably, step (a) is effected in the absence of the indicated factors (i.e., Wnt inhibitor, bFGF, IGF1 and a GSK3 inhibitor). In one embodiment, the medium throughout the differentiation process is devoid of a member of the TGFβ superfamily (e.g., activin A) at a concentration promoting the differentiation of photoreceptor cells. In another embodiment, the level of TGFβ superfamily member in the medium is less than 20 ng/ml, 10 ng/ml, 1 ng/ml or even less than 0.1 ng/ml.

It will be appreciated that the factors can be added in a sequential manner e.g., NA (day 0-day 30), followed by NA+bFGF (day 3-day 60), followed by NA+bFGF+GSK3 inhibitor (e.g., CHIR) (day 10-day 60) or NA+ GSK3 inhibitor (day 10-day 60) or bFGF+GSK3 inhibitor (day 10-day 60).

According to some embodiments, culturing or differentiation may include the use of human serum albumin (HSA). In some embodiments, HSA is provided at a concentration of between about 0.5% to about 1%. In some embodiments, the HSA is provided at a concentration of between about 0.01% to about 10%. In other embodiments, HSA is provided at a concentration of about, for example, 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2.0%, 2.5%, 3%, 3.5%, 4%, 4.5%, or 5.0%.

According to a specific embodiment, the culturing of step (a) i.e., NA without the additional factors is effected under adherent conditions and the culturing of step (b) i.e., NA+factors is effected under adherent conditions.

According to a specific embodiment, the culturing of step (a) i.e., NA without the additional factors is effected under non-adherent conditions and the culturing of step (b) i.e., NA+factors is effected under non-adherent conditions.

According to a specific embodiment, the culturing of step (a) i.e., NA without the additional factors is effected under non-adherent conditions and the culturing of step (b) i.e., NA+factors is effected under adherent conditions.

According to a specific embodiment, the culturing of step (a) i.e., NA without the additional factors is effected under adherent conditions and the culturing of step (b) i.e., NA+factors is effected under non-adherent conditions.

An embodiment of the above described protocol is described in further detail, with additional embodiments in the Examples section which follows.

When pluripotent stem cells are plated onto a non-adherent substrate (e.g., cell culture plate), the cell culture may be referred to as a cell suspension or spheroid body (SB), preferably free floating clusters in a suspension culture, i.e., aggregates of cells derived from human embryonic stem cells (hESCs). The cell clusters do not adhere to any substrate (e.g., culture plate, carrier). Sources of free floating stem cells were previously described in WO 06/070370, which is herein incorporated by reference in its entirety. This stage may be effected for a minimum of 1 day, more preferably two days, three days, 1 week or even 14 days. According to a specific embodiment, this stage is effected for 3-6 days (see FIG. 2). According to one embodiment, when the cells are cultured on the non-adherent substrate e.g., cell culture plates, the atmospheric oxygen conditions are 20%. However, manipulation of the atmospheric oxygen conditions is also contemplated such that the atmospheric oxygen percent is less than about 20%, 15%, 10%, 9%, 8%, 7%, 6% or even less than about 5% (e.g., between 1%-20%, 1%-10% or 0-5%).

According to a particular embodiment, the cells are cultured on the non-adherent substrate initially under normal atmospheric oxygen conditions and then lowered to less than normal atmospheric oxygen conditions.

Examples of non-adherent cell culture plates include those manufactured by Nunc (e.g., HYDROCELL™; Cat No. 174912).

Typically, the clusters comprise at least 50-500,000, 50-100,000, 50-50,000, 50-10,000, 50-5000, 50-1000 cells. According to one embodiment, the cells in the clusters are not organized into layers and form irregular shapes. In one embodiment, the clusters are devoid of pluripotent embryonic stem cells. In another embodiment, the clusters comprise small amounts of pluripotent embryonic stem cells (e.g., no more than 5%, or no more than 3% (e.g., 0.01-2.7%) cells that co-express OCT4 and TRA 1-60 at the protein level). Typically, the clusters comprise cells that have been partially differentiated under the influence of nicotinamide. Such cells primarily express neural and retinal precursor markers such as PAX6, Six6, Rx, Six3 and/or CHX10.

The clusters may be dissociated using enzymatic or non-enzymatic methods (e.g., mechanical, chemical) known in the art. According to one embodiment, the cells are dissociated such that they are no longer in clusters—e.g., aggregates or clumps of 2-100,000 cells, 2-50,000 cells, 2-10,000 cells, 2-5,000 cells, 2-1,000 cells, 2-500 cells, 2-100 cells, 2-50 cells. According to a particular embodiment, the cells are in a single cell suspension.

The basic medium in which the ESCs are differentiated is any known cell culture medium known in the art for supporting cells growth in vitro, typically, a medium comprising a defined base solution, which includes salts, sugars, amino acids and any other nutrients required for the maintenance of the cells in the culture in a viable state. According to a specific embodiment, the basic medium is not a conditioned medium. Non-limiting examples of commercially available basic media that may be utilized in accordance with the disclosure comprise NUTRISTEM® (without TGFβ for ESC differentiation, with bFGF and TGFβ for ESC expansion) Neurobasal™, KO-DMEM, DMEM, DMEM/F12, Cellgro™ Stem Cell Growth Medium, or X-Vivo™. The basic medium may be supplemented with a variety of agents as known in the art dealing with cell cultures. The following is a non-limiting reference to various supplements that may be included in the culture system to be used in accordance with the present disclosure:

serum or with a serum replacement containing medium, such as, without being limited thereto, knock out serum replacement (KOSR), NUTRIDOMA-CS™, TCH™, N2, N2 derivative, or B-27™ or a combination;
  an extracellular matrix (ECM) component, such as, without being limited thereto, fibronectin, laminin, collagen and gelatin. The ECM may then be used to carry the factors as described herein (i.e., bFGF, IGF1, Wnt inhibitor, GSK3 inhibitor);
  an antibacterial agent, such as, without being limited thereto, penicillin and streptomycin;
  non-essential amino acids (NEAA), neurotrophins which are known to play a role in promoting the survival of SCs in culture, such as, without being limited thereto, BDNF, NT3, NT4.

According to a preferred embodiment, the medium used for differentiating the ESCs is NUTRISTEM® medium (e.g., Biological Industries, 06-5102-01-1A).

According to a particular embodiment, differentiation and expansion of ESCs is effected under xeno free conditions.

According to one embodiment, the proliferation/growth medium is devoid of xeno contaminants, i.e., free of animal derived components such as serum, animal derived growth factors and albumin. Thus, according to this embodiment, the culturing is performed in the absence of xeno contaminants.

Other methods for culturing ESCs under xeno free conditions are provided in U.S. Patent Application Publication No. 20130196369, the contents of which are herein incorporated by reference in their entirety.

The preparations comprising photoreceptor cells may be prepared in accordance with Good Manufacturing Practices (GMP) (e.g., the preparations are GMP-compliant) and/or current Good Tissue Practices (GTP) (e.g., the preparations may be GTP-compliant).

During differentiation steps, the embryonic stem cells may be monitored for their differentiation state. Cell differentiation can be determined upon examination of cell or tissue-specific markers which are known to be indicative of differentiation. Tissue/cell specific markers can be detected using immunological techniques well known in the art [Thomson J A et al., (1998). Science 282: 1145-7]. Examples include, but are not limited to, flow cytometry for membrane-bound or intracellular markers, immunohistochemistry for extracellular and intracellular markers and enzymatic immunoassay, for secreted molecular markers.

Once the cells are differentiated into photoreceptor cells, they may be expanded.

The present inventor has shown that cells removed from the culture system following the differentiation process described herein express markers of photoreceptors. Such cells may be used to treat retinal disorders.

Optionally, the photoreceptors may be cultured so as to obtain greater numbers of photoreceptor cells (i.e., expanded). Care should be taken during the expansion phase that conditions therein do not promote expansion of RPE cells over photoreceptor cells. In one embodiment, the culturing enriches for the photoreceptor cells. Thus, for example, in one embodiment, no more than about 5%, 10%, 15%, 20% of the cells which are expanded are RPE cells. According to another embodiment, between about 5-90% of the cells which are expanded are RPE cells. According to another embodiment between about 5-80% of the cells which are expanded are RPE cells. According to another embodiment between 5-70% of the cells which are expanded are RPE cells. According to another embodiment between 5-60% of the cells which are expanded are RPE cells. According to another embodiment between 5-50% of the cells which are expanded are RPE cells. According to another embodiment, between 10-50% of the cells which are expanded are RPE cells. According to another embodiment, between 20-50% of the cells which are expanded are RPE cells. According to another embodiment, between 30-50% of the cells which are expanded are RPE cells. According to another embodiment, between 10-40% of the cells which are expanded are RPE cells. According to another embodiment, between 10-30% of the cells which are expanded are RPE cells. According to another embodiment, between 10-20% of the cells which are expanded are RPE cells.

Expansion of the enriched population of cells comprising photoreceptors may be effected on an extra cellular matrix, e.g., gelatin, collagen I, collagen IV, laminin (e.g., laminin 521), fibronectin or poly-D-lysine.

In one embodiment, the expanding is effected in the presence of nicotinamide (e.g., between about 0.5-100 mM).

The enriched population of photoreceptor cells may be expanded in suspension (with or without a micro-carrier) or in a monolayer. The expansion of the enriched population of photoreceptor cells in monolayer cultures or in suspension culture may be modified to large scale expansion in bioreactors or multi/hyper stacks by methods well known to those versed in the art.

According to one embodiment, the expansion phase is effected for at least one week, at least 2 weeks, at least 3 weeks, at least 4 weeks, at least 5 weeks, at least 6 weeks, at least 7 weeks, at least 8 weeks, at least 9 weeks or even 10 weeks. Preferably, the expansion phase is effected for 1 week-10 weeks, more preferably 2 weeks-10 weeks, more preferably, 3 weeks-10 weeks, more preferably 4 weeks-10 weeks, or 4 weeks-8 weeks.

According to still another embodiment, the enriched population of photoreceptor cells are passaged at least 1 time during the expansion phase, at least twice during the expansion phase, at least three times during the expansion phase, at least four times during the expansion phase or at least five times during the expansion phase or at least six times during the expansion phase.

The population of photoreceptor cells generated according to the methods described herein may be characterized according to a number of different parameters.

Thus, for example, the photoreceptor cells obtained may be with an elongated cell body and an apex of cytoplasm.

Harvesting of the expanded population of photoreceptor cells may be effected using methods known in the art (e.g., using an enzyme such as trypsin, EDTA).

Following harvesting, the populations of photoreceptors cells may optionally be cryopreserved using methods known in the art. Examples of media suitable for cryopreservation include but are not limited to 90% Human Serum/10% DMSO, CRYOSTOR™ 10%, 5% and 2%, STEM-CELL-BANKER™ and PRIME-XV™ FreezIS.

It will be appreciated that the cell populations disclosed herein are devoid of undifferentiated human embryonic stem cells. According to one embodiment, less than 1:250,000 cells are Oct4$^+$TRA-1-60$^+$ cells, as measured for example by FACS. The cells also have down-regulated (by more than 5,000 fold) expression of GDF3 or TDGF as measured by PCR.

The photoreceptor cells of this aspect of the present disclosure do not express embryonic stem cell markers. Said one or more embryonic stem cell markers may be OCT-4, NANOG, SSEA-3, SSEA-4, TRA-1-60, and/or TRA-1-81.

The photoreceptor preparations may be substantially enriched, with respect to non-photoreceptor cells, comprising at least about 50%, 75%, 80%, 85%, 90%, 91%, 92%, 93%, 94%, 95%, 96%, 97%, 98%, 99%, or 100% photoreceptor cells. The photoreceptor cell preparation may be essentially free of RPE cells or consist of photoreceptor cells. For example, the substantially enriched preparation of photoreceptor cells may comprise less than about 50% 25%, 20%, 15%, 10%, 9%, 8%, 7%, 6%, 5%, 4%, 3%, 2%, or 1% non-photoreceptor cell type, for example RPE cells. For example, the photoreceptor cell preparation may comprise less than about 50% 25%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% non-photoreceptor cells, for example RPE cells.

The preparations described herein may be substantially free of bacterial, viral, or fungal contamination or infection, including but not limited to the presence of HIV I, HIV 2, HBV, HCV, HAV, CMV, HTLV 1, HTLV 2, parvovirus B19, Epstein-Barr virus, or herpesvirus 1 and 2, SV40, HHV5, 6, 7, 8, CMV, polyoma virus, HPV, Enterovirus. The preparations described herein may be substantially free of mycoplasma contamination or infection.

Another way of characterizing the cell populations disclosed herein is by marker expression. Thus, for example, at least 30%, 40%, 45%, 50%, 55%, 60%, 65%, 70%, 75%, 80%, 85%, 90%, 91%, 92%, 93%, 94%, 95%, 96%, 97%, 98%, 99%, or 100% of the cells express RAX, as measured by immunostaining. According to one embodiment, between about 70-100% of the cells express RAX. Preferably, the level of RAX expressed by the cells is at least 2 fold greater, 5 fold greater or even 10 fold greater than the level of expression in RPE cells or non-differentiated ESCs, as measured by RT-PCR.

According to another embodiment, at least 30%, 40%, 45%, 50%, 55%, 60%, 65%, 70%, 75%, 80%, 85%, 90%, 91%, 92%, 93%, 94%, 95%, 96%, 97%, 98%, 99%, or 100% of the cells express CHX10, as measured by immunostaining. For example, between about 70-100% of the cells express CHX10. Preferably, the level of CHX10 expressed by the cells is at least 2 fold greater, 5 fold greater or even 10 fold greater than the level of expression in RPE cells or non-differentiated ESCs, as measured by RT-PCR.

According to another embodiment, at least about 30%, 50%, 70%, 80%, 85%, 87%, 89%, 90%, 95%, 97% or 100% of the cells express rhodopsin, as measured by immunostaining. Preferably, the level of rhodopsin expressed by the cells is at least 2 fold greater, 5 fold greater or even 10 fold greater than the level of expression in RPE cells or non-differentiated ESCs, as measured by RT-PCR.

According to another embodiment, at least about 30%, 40%, 45%, 50%, 55%, 60%, 65%, 70%, 75%, 80%, 85%, 90%, 91%, 92%, 93%, 94%, 95%, 96%, 97%, 98%, 99%, or 100% of the cells express neural retina-specific leucine zipper protein (NRL), as measured by immunostaining. For example, between about 70-100% of the cells express NRL by immunostaining. Preferably, the level of NRL expressed by the cells is at least 2 fold greater, 5 fold greater or even 10 fold greater than the level of expression in RPE cells or non-differentiated ESCs, as measured by RT-PCR.

Preferably, the cells of this aspect of the present invention do not express markers of RPE cells. Accordingly, following the differentiation stage (and optionally expansion) the photoreceptors cells may be isolated from the culture. According to a specific embodiment, the photoreceptor cell preparation is isolated such that there are no RPE cells, or less than 40%, 30%, 25%, 20%, 15%, 10% 5% RPE cells in the isolated preparation. Thus, for example, preferably the cells do not express (or less than about 40%, 35%, 30%, 25%, 20%, 15%, 10%, 9%, 8%, 7%, 6%, 5%, 4%, 3%, 2%, or 1% of the cells express) MITF, RPE65, bestrophin 1, premelanosome protein (PMEL17) or CRALBP. Preferably, the level of RPE markers expressed by the cells is at least 2 fold less, 5 fold less or even 10 fold less than the level of expression in RPE cells, as measured by RT-PCR.

It would be well appreciated by those versed in the art that the derivation of photoreceptor cells is of great benefit. They may be used as an in vitro model for the development of new drugs to promote their survival, regeneration and function. Photoreceptor cells may serve for high throughput screening for compounds that have a toxic or regenerative effect on photoreceptor cells. They may be used to uncover mechanisms, new genes, soluble or membrane-bound factors that are important for the development, differentiation, maintenance, survival and function of photoreceptor cells.

The photoreceptor cells may also serve as an unlimited source of photoreceptor cells for transplantation, replenishment and support of malfunctioning or degenerated photoreceptor cells in retinal degenerations. Furthermore, genetically modified photoreceptor cells may serve as a vector to carry and express genes in the eye and retina after transplantation.

Eye conditions for which the photoreceptor cells may serve as therapeutics include, but are not limited to retinal diseases or disorders generally associated with retinal dysfunction, retinal injury, and/or loss of photoreceptor function. A non-limiting list of conditions which may be treated comprises retinitis pigmentosa, lebers congenital amaurosis, hereditary or acquired macular degeneration, age related macular degeneration (AMD), dry AMD, Best disease, retinal detachment, gyrate atrophy, choroideremia, pattern dystrophy as well as other dystrophies of the RPE, Stargardt disease, RPE and retinal damage due to damage caused by any one of photic, laser, inflammatory, infectious, radiation, neo vascular or traumatic injury.

The present inventors further contemplate use of the photoreceptor cells for treatment of other diseases such as neurodegenerative diseases including but not limited to Parkinson's, ALS, Multiple Sclerosis, Huntingdon's disease, autoimmune encephalomyelitis, diabetic neuropathy, Alzheimer's and epilepsy.

Subjects which may be treated include primate (including humans), canine, feline, ungulate (e.g., equine, bovine, swine (e.g., pig)), avian, and other subjects. Humans and non-human animals having commercial importance (e.g., livestock and domesticated animals) are of particular interest. Exemplary mammals which may be treated include, canines; felines; equines; bovines; ovines; rodentia, etc. and primates, particularly humans. Non-human animal models, particularly mammals, e.g., primate, murine, lagomorpha, etc. may be used for experimental investigations.

The photoreceptor cells generated as described herein may be transplanted to various target sites within a subject's eye. In accordance with one embodiment, the transplantation of the photoreceptor cells is to the subretinal space of the eye. In addition, because of the migratory ability and/or positive paracrine effects of the cells, transplantation into additional ocular compartments can be considered including the vitreal space, inner or outer retina, the retinal periphery and within the choroids.

The number of photoreceptor cells that may be administered to the subject are typically between at least about 5,000 and about $5 \times 10^6$ viable cells per dose. In some embodiments, the photoreceptor cell composition comprises at least 100,000 viable cells. In some embodiments, the photoreceptor cell composition comprises at least 150,000 viable cells. In some embodiments, the photoreceptor cell composition comprises at least 200,000 viable cells. In some embodiments, the photoreceptor cell composition comprises at least 250,000 viable cells. In some embodiments, the photoreceptor cell composition comprises at least 300,000 viable cells. In some embodiments, the photoreceptor cell composition comprises at least 350,000 viable cells. In some embodiments, the photoreceptor cell composition comprises at least 400,000 viable cells. In some embodiments, the photoreceptor cell composition comprises at least 450,000 viable cells. In some embodiments, the photoreceptor cell composition comprises at least 500,000 viable cells. In some embodiments, the photoreceptor cell composition comprises at least 600,000, at least 700,000, at least 800,000, at least 900,000, at least 1,000,000, at least, 2,000,000, at least 3,000,000, at least, 4,000,000, at least 5,000,000 at least 6,000,000, at least 7,000,000, at least 8,000,000, at least 9,000,000, at least 10,000,000, at least 11,000,000, or at least 12,000,000 viable cells.

The cells may be formulated in a carrier (e.g., an isotonic solution and/or a saline) such as BSS PLUS™. Other contemplated solutions include cryopreservation solutions such as CRYOSTOR™ 5 or CRYOSTOR™ 2. The carrier may optionally comprise additional factors that support photoreceptor and RPE engraftment, integration, survival, and potency.

The transplantation may be performed by various techniques known in the art. Methods for performing retinal cell transplants are described in, for example, U.S. Pat. Nos. 5,962,027, 6,045,791, and 5,941,250 and in Eye Graefes Arch Clin Exp Opthalmol March 1997; 235(3):149-58; Biochem Biophys Res Commun Feb. 24, 2000; 268(3): 842-6; Opthalmic Surg February 1991; 22(2): 102-8. Methods for performing corneal transplants are described in, for example, U.S. Pat. No. 5,755,785, and in Eye 1995; 9 (Pt 6 Su):6-12; Curr Opin Opthalmol August 1992; 3 (4): 473-81; Ophthalmic Surg Lasers April 1998; 29 (4): 305-8; Ophthalmology April 2000; 107 (4): 719-24; and Jpn J Ophthalmol November-December 1999; 43(6): 502-8. If mainly paracrine effects are to be utilized, cells may also be delivered and maintained in the eye encapsulated within a semi-permeable container, which will also decrease exposure of the cells to the host immune system.

The step of administering may comprise intraocular administration of the photoreceptor cells into an eye in need thereof. The intraocular administration may comprise injection of the photoreceptor cells into the subretinal space.

In accordance with one embodiment, transplantation is performed via pars plana vitrectomy surgery followed by delivery of the cells through a small retinal opening into the sub-retinal space or by direct injection.

The photoreceptor cells may be transplanted in various forms. For example, the photoreceptor cells may be introduced into the target site in the form of single cell suspension, with matrix or adhered onto a matrix or a membrane, extracellular matrix or substrate such as a biodegradable polymer or a combination. The photoreceptor cells may also be transplanted together (co-transplantation) with other retinal cells, such as with RPE cells.

The effectiveness of treatment may be assessed by different measures of visual and ocular function and structure, including, among others, best corrected visual acuity (BCVA), retinal sensitivity to light as measured by perimetry or microperimetry in the dark and light-adapted states, full-field, multi-focal, focal or pattern electroretinography ERG), contrast sensitivity, reading speed, color vision, clinical biomicroscopic examination, fundus photography, optical coherence tomography (OCT), fundus auto-fluorescence (FAF), infrared and multicolor imaging, fluorescein or ICG angiography, adoptive optics and additional means used to evaluate visual function and ocular structure.

The subject may be administered corticosteroids prior to or concurrently with the administration of the photoreceptor cells, such as prednisolone or methylprednisolone, PRED FORTE™.

According to another embodiment, the subject is not administered corticosteroids prior to or concurrently with the administration of the photoreceptor cells, such as prednisolone or methylprednisolone, PRED FORTE™.

Immunosuppressive drugs may be administered to the subject prior to, concurrently with and/or following treatment.

The immunosuppressive drug may belong to the following classes:

Glucocorticoids, Cytostatics (e.g., alkylating agent or antimetabolite), antibodies (polyclonal or monoclonal), drugs acting on immunophilins (e.g., ciclosporin, Tacrolimus or Sirolimus). Additional drugs include interferons, opioids, TNF binding proteins, mycophenolate and small biological agents.

Examples of immunosuppressive drugs include: mesenchymal stem cells, anti-lymphocyte globulin (ALG) polyclonal antibody, anti-thymocyte globulin (ATG) polyclonal antibody, azathioprine, BAST L1X1MAB® (anti-I L-2Ra receptor antibody), cyclosporin (cyclosporin A), DACLIZUMAB® (anti-I L-2Ra receptor antibody), everolimus, mycophenolic acid, RITUX1MAB® (anti-CD20 antibody), sirolimus, tacrolimus, Tacrolimus and or Mycophenolate mofetil.

Antibiotics may be administered to the subject prior to, concurrently with and/or following treatment. Examples of antibiotics include Oflox, Gentamicin, Chloramphenicol, Tobrex, Vigamox or any other topical antibiotic preparation authorized for ocular use.

In certain embodiments, photoreceptors formulated for administration to a subject may comprise one or more immunosuppressive compounds or antibiotics that are formulated for slow release of the one or more immunosuppressive compounds or antibiotics.

Alternatively, the photoreceptor cell composition may be administered without the use of immunosuppressive drugs.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al., (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al., (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839, 153; 3,850,752; 3,850,578; 3,853,987; 3,867,517; 3,879, 262; 3,901,654; 3,935,074; 3,984,533; 3,996,345; 4,034, 074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Generation of Photoreceptor Cells

Figure 1:
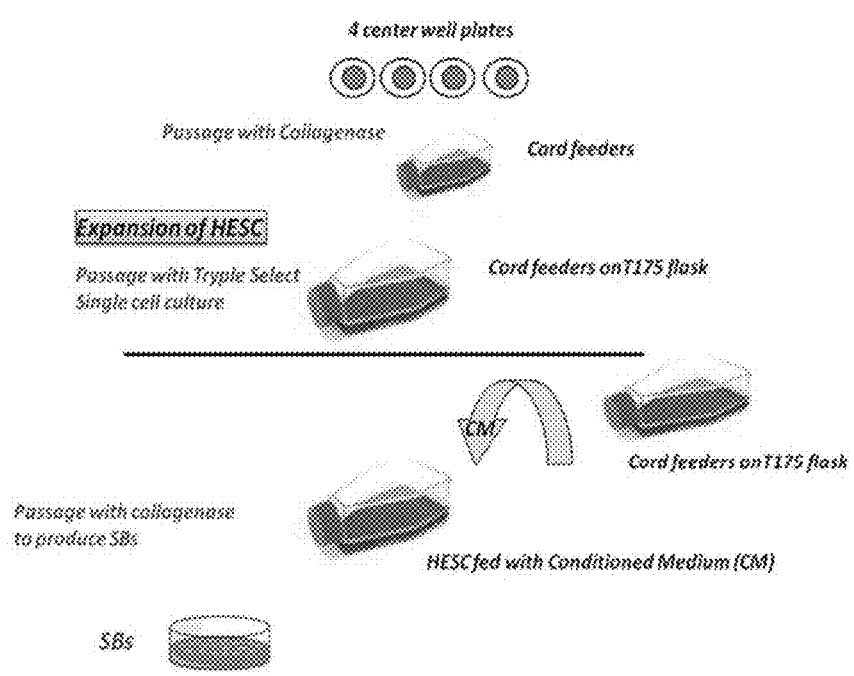

In preparation of conditioned medium, T75 flasks were seeded with irradiated cord cells ($2.3 \times 10^6$ w/o gelatin) in DMEM+20% Human serum medium. After 5-24 hr, the medium was replaced with NUTRISTEM® (NU-TRISTEM® hPSC XF*Xeno-free medium for Human Pluripotent Stem Cells, Biological Industries) for conditioning. After 16 to 72 hours of conditioning, the medium was harvested and replaced by fresh medium. According to this methodology, sequential conditioning of medium may be performed 3 to 4 times per week.

hESCs were expanded by harvesting cells from four center-well plates using collagenase and plated in T75 or T25 flasks pre-seeded with cord feeders (0.66 and $2.3 \times 10^6$ feeders per T25 and T75 flasks, respectively). Following one week of culture in NUTRISTEM®, hESCs were harvested with TRYPLE™ Select (diluted 1:1 with PBS in some instances) and split, seeding $2 \times 10^6$ hESC per T175 flask, pre-seeded with cord feeders ($5 \times 10^6$ per flask). An illustration of this process is shown in FIG. 1.

For transfer to feeder-free culture in conditioned medium, the hESCs, after one-week of culture in T175 flasks, were harvested using collagenase A, and a quarter of them were seeded into feeder-free T175 flask and cultured in conditioned medium. After 7 days, hESC colonies filled the flask and were harvested with collagenase A.

Alternatively, hESCs that grew on cord feeders were harvested with TRYPLE™ Select cell dissociation reagent and seeded on T75 flasks pre-coated with laminin 521 (BioLamina). hESCs seeding density was between $2$-$4 \times 10^6$ per flask. Following 5 to 6 days, the hESCs were harvested using collagenase A and plated to form spheroid bodies (SBs) in non-adherent conditions (HYDROCELL™ dishes or NUNCLON™ SPHERA™ dishes; Thermo Scientific).

SBs were generated under non-adherent conditions (day 0) from cord-feeder-conditioned media culture systems, or from feeder free laminin 521 culture systems, as described above. SBs were cultured in the following medium: NUTRISTEM® minus medium (Biological industries, Beit Haemek, Israel) supplemented with 50 U/ml penicillin and 50 μg/ml streptomycin (Gibco-BRL, Carlsbad, Calif.). In the initial 0 to 6 days of SBs culture (under non-adherent conditions), the medium was supplemented with 10 mM nicotinamide (Sigma, St. Louis, Mo.). It was further supplemented with the addition of the following factors in different combinations: 10 mM nicotinamide (Sigma, St. Louis, Mo.), 3 μM endo-IWR 1 (IWR1e; TOCRIS, a biotechne brand, Minneapolis, Minn.), 20 ng/ml bFGF (PeproTech Inc., Rocky Hill, N.J.), 5 ng/ml IGF1 (R&D Systems Inc., Minneapolis, Minn.) and 3 μM CHIR99021 (CHIR; PeproTech Inc., Rocky Hill, N.J.). Various combinations of the following supplements were also evaluated: 0.5-1% HSA (Albumin 25%, Octapharma, Elersvagen, Sweden), 1% MATRIGEL™ (growth-factor-reduced; BD Biosciences), 1-10 μg/ml Laminin 511 and/or 521 (BioLamina, Sundbyberg, Sweden), 3-10 μg/ml Collagen human (Sigma St. Louis Mo.) for 2 to 8 weeks.

Example 2

Expression of Eye Field Markers, Retinal Progenitor Markers and Photoreceptor Progenitor Cell Markers in SBs of hESC-Derived Photoreceptor Progenitor Cells Real-time PCR was used to determine the expression of eye field and retinal progenitor markers and photoreceptor progenitor markers. mRNA was extracted using QUICK-RNA Micro Prep, Zymo Research (Cat #R1051) and the RT reaction was accomplished with QSCRIPT™ reverse transcriptase (Quanta BioScience Inc., Gaithersburg, Md.). The levels of transcripts were monitored using commercially available TAQMAN™ Assay-on-Demand Gene Expression Products (Applies Biosystems, Foster City, Calif.). The expression of eye field and photoreceptor precursor markers were analyzed at time points of 14 days to 8 weeks. At Time point 0 (T0), the derivation of SBs and the beginning of their culture in non-adherent culture dishes were initiated.

The TAQMAN® Assays-on-Demand (Applied Biosystems, Foster City, CA): Pax6, assay ID Hs00240871_m1; Six3, assay ID Hs00193667_m1; Rx1, assay ID Hs00429459_m1; Chx10, assay ID Hs01584047_m1; Crx, assay ID Hs00230899_m1; Nr1, assay ID Hs00172997_m1; Rho, assay ID Hs00892431_m1; Six6, assay ID Hs00201310_m1; GusB, assay ID Hs00939627_m1 primers were used in the analysis.

Figure 2:
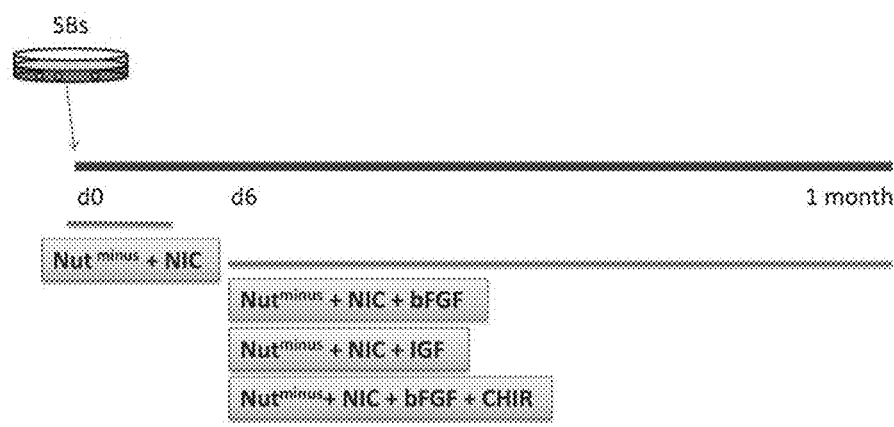
Figure 3:
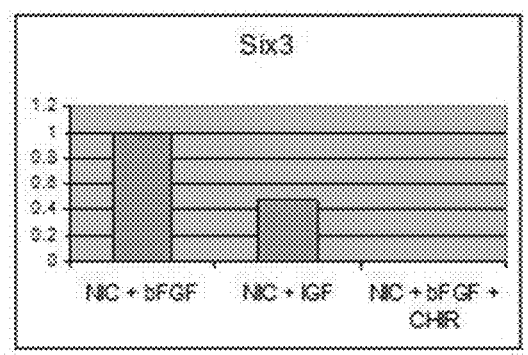
Figure 4:
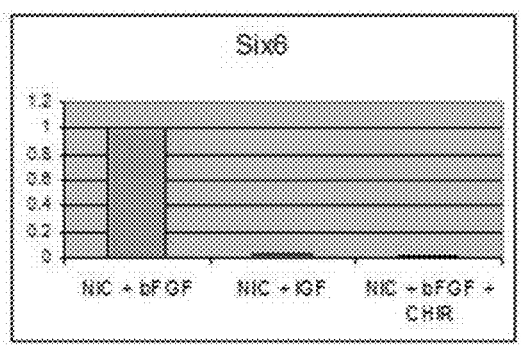
Figure 5:
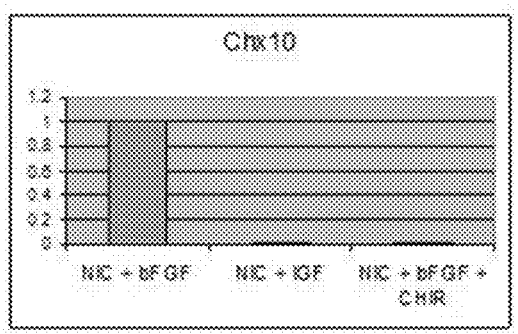
Figure 6:
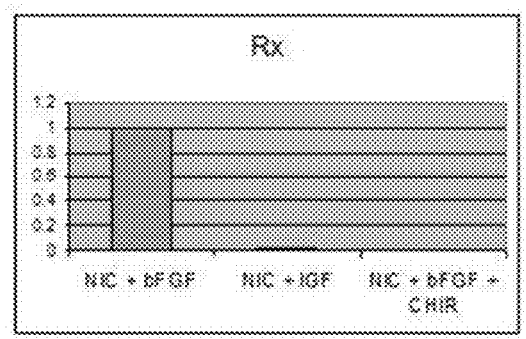
Figure 11:
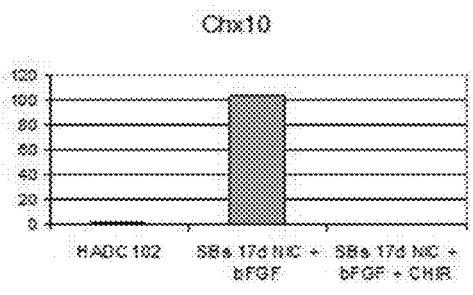

SBs were treated with combinations of NIC, bFGF, CHIR and IGF1 for 1 month. Alternatively, the SBs were cultured in the presence of combinations of NIC, bFGF, and CHIR for 17 days, as shown in FIG. 2. At the end of these culture periods, the expression of eye field and retinal progenitor markers (Rx, Six3, Six6, Chx10) and photoreceptor progenitor markers (NRL, CRX) was analyzed by Real-time PCR. As shown in FIG. 3 through FIG. 14, treatment with NIC combined with bFGF or IGF1 induced differentiation into cells expressing eye field markers as well as photoreceptor progenitor markers. FIG. 3 through FIG. 8 show graphs illustrating marker expression of Six3, Six6, Chx10, Rx, CRX, and NRL, respectively, in SBs cultured in NIC+bFGF or NIC+IGF or NIC+bFGF+CHIR for 4 weeks. Relative quantity of gene expression is plotted against different conditions. FIG. 9 through FIG. 14 show graphs illustrating marker expression of Six3, Six6, Chx10, Rx, CRX, and NRL, respectively, in SBs cultured in NIC+bFGF or NIC+bFGF+CHIR for 17 days. The control, HADC102, was comprised of undifferentiated HAD-C102 cells cultured for 6-7 days in NUTRISTEM® hPSC XF*Xeno-free medium for Human Pluripotent Stem Cells (Biological Industries).

The combination of NIC+bFGF+CHIR induced the expression of photoreceptor progenitor markers. The expression of the eye field and retinal progenitor markers, Rx, Six3, Six6 and Chx10 was highest in this assay when SBs were cultured in the presence of NIC+bFGF after 17 days and after 1 month of differentiation. The expression of the photoreceptor progenitor marker, NRL, was the highest in this assay when SBs were cultured in the presence of NIC+bFGF for 1 month and the expression of the photoreceptor progenitor marker, Crx, was highest when SBs were cultured in the presence of NIC and bFGF for 17 days. The elevation of the expression of these markers, particularly Crx, demonstrates the differentiation towards the photoreceptor fate. The results described in the present disclosure show that SBs treated in vitro either with NIC+bFGF+CHIR or with NIC+IWR1e+HSA gave rise to cells that express markers of mature photoreceptors rhodopsin and red/green opsin in vivo.

SBs were also treated with different combinations of NIC, IWR1e and bFGF for 3 weeks. FIG. 15 provides an illustration of the timeline and agents that were analyzed. The expression of eye field and retinal progenitor markers was analyzed following 20 days of differentiation. FIG. 16 through FIG. 20 show graphs illustrating the expression of eye field and retinal progenitor markers, Pax6, Six3, Rx, Six6, and Chx10, respectively, after SBs were cultured in NIC for 20 days. The control, HAD102, was comprised of undifferentiated HAD-C102 cells cultured for 6-7 days in NUTRISTEM® hPSC XF*Xeno-free medium for Human Pluripotent Stem Cells (Biological Industries). Results demonstrate the ability of NIC to generate hESC-derived photoreceptor progenitors.

FIG. 21 through FIG. 25 show graphs illustrating the expression of eye field and retinal progenitor markers, Pax6, Six3, Rx, Six6, and Chx10, respectively, after SBs were cultured in either NIC+IWR1e or NIC+IWR1e+bFGF or NIC+bFGF for 20 days. The control, HAD102, was comprised of undifferentiated HAD-C102 cells cultured for 6-7 days in NUTRISTEM® hPSC XF*Xeno-free medium for Human Pluripotent Stem Cells (Biological Industries). These results demonstrate that IWR1e also induced the expression of markers of hESC-derived photoreceptor progenitors. FIG. 26 through FIG. 35 show graphs illustrating the expression of eye field and retinal progenitor markers, Pax6, Six3, Rx, Six6, and Chx10, respectively, after SBs were cultured in either NIC+IWR1e or NIC or IWR1e or IWR1e+bFGF. The control, HAD102, was comprised of undifferentiated HAD-C102 cells cultured for 6-7 days in NUTRISTEM® hPSC XF*Xeno-free medium for Human Pluripotent Stem Cells (Biological Industries). As shown, the highest expression of the eye field and retinal progenitor markers, Pax6, Rx, Six3, Six6 and Chx10 was demonstrated when SBs were differentiated in the presence of NIC combined with IWR1e. The expression level of these markers was much lower when the cells were cultured with IWR1e alone.

The addition of HSA to the culture medium of the SBs was also analyzed. FIG. 36 provides an illustration of the timeline and agents that were analyzed. The quantity of SBs that were generated was increased with the addition of HSA. In addition, the SBs obtained were larger and more compacted, as shown in FIG. 37A and FIG. 37B, with the addition of HSA to the SBs culture medium. The results indicate that the addition of HSA improves the yield of retinal progenitor cells and also the efficiency of differentiation.

The expression of eye field and retinal progenitor markers in SBs was analyzed following 4 weeks of differentiation. FIG. 38 through FIG. 41 show graphs illustrating the expression of eye field and retinal progenitor markers, Chx10, Pax6, Rx, and Six6, respectively, after SBs were cultured in either NIC+IWRe+HSA or NIC+IWRe for 4 weeks, and undifferentiated HAD-C102 cells as a control. FIG. 42 through FIG. 45 show graphs illustrating the expression of eye field and retinal progenitor markers, Chx10, Pax6, Rx, and Six6, respectively, after SBs were cultured in either NIC+bFGF or NIC+HSA or NIC+IWRe+HSA for 4 weeks, and undifferentiated HAD-C102 cells (HAD102) as a control. The highest expression of the eye field and retinal progenitor markers, Chx10, Pax6, Rx, and Six6 was demonstrated when SBs were differentiated in the presence of NIC combined with IWR1e and HSA (NIH).

The effect of NIH was further tested after time periods of between 4.5 and 7 weeks of incubation in its presence. FIG. 46 through FIG. 49 show graphs illustrating the expression of eye field and retinal progenitor markers, Chx10, Pax6, Rx, and Six6, respectively, after SBs were cultured in either NIH for 4.5 weeks or NIH for 5 weeks or NIH for 6 weeks or NIH for 7 weeks, and undifferentiated cells from the HAD-C102 cell line. The highest level of expression of the markers Rx, Chx10 and Six6 was obtained after 7 weeks of incubation in the presence of NIH.

To analyze the effect that different culture systems had on the expression of eye field and photoreceptor progenitor markers, expression levels of SBs that were derived from hESCs cultured on gelatin in NUTRISTEM® hPSC XF*Xeno-free medium for Human Pluripotent Stem Cells, (Biological Industries) conditioned by Cord-feeders (NIH (cord)) were compared with expression levels of SBs derived from hESCs cultured on laminin 521 in the same medium (NUTRISTEM® hPSC XF*Xeno-free medium for Human Pluripotent Stem Cells, (NIH (Lam)). As a control, SBs derived from hESC that were cultured on gelatin in NUTRISTEM® hPSC XF*Xeno-free medium for Human Pluripotent Stem Cells conditioned by cord feeders and cultured overnight in suspension in the presence of NIC (SBs NIC) were used.

FIG. 50 through FIG. 54 show graphs illustrating the expression of eye field and retinal progenitor markers, Rx, Pax6, Six3, Six6, and Chx10, respectively, after SBs were cultured in NIH for 5 weeks (NIH (cord)). NIH (cord) represents SBs derived from hESCs cultured with cord feeder conditioned medium. NIH (Lam) represents SBs derived from hESC cultured on laminin 521. SBs NIC represents the control, which comprised SBs that were derived from hESC cultured with cord feeder conditioned medium in suspension overnight with NIC.

FIG. 55 through FIG. 58 show a set of graphs from an additional analysis illustrating the expression of eye field and retinal progenitor markers, Rx, Pax6, Six6, and Chx10, respectively, after SBs were cultured in NIH for 5 weeks NIH (cord), NIH (Lam) and control (SBs NIC). Culturing HAD-C102 cells on Laminin 521 may be preferable compared to conditioned medium because the culturing process is more defined and controlled. In addition, the expression of all the markers analyzed was higher when SBs were produced from hESCs cultured on Laminin 521. Under these conditions (Laminin 521), the manufacture process was also more efficient. Unexpectedly, the initial culturing of hESC on laminin 521 gave rise to a more efficient differentiation result when compared to initial culturing of the hESCs on gelatin in feeder cell conditioned medium.

Example 3

Protein Expression

The expression of eye field and retinal progenitor cell markers at the protein level was analyzed using immuno-fluorescence staining. To characterize the immunophenotype of cells within the aggregates, spheroid bodies (SBs) that were cultivated for 4 to 8 weeks were partially disaggregated by mechanical means, and the resulting small clumps and single cells were plated in the same medium as in the suspension on poly-D-lysine (30-70 kDa, 10 μg/ml) and laminin (4 μg/ml). The cells were differentiated in the same medium for up to 2 weeks. The cells were then fixed with 4% paraformaldehyde for 20 minutes at room temperature. After washing with PBS, specimens were blocked for 1 hour at room temperature with PBS solution containing 5% normal donkey serum and 0.2% TRITON™ and incubated for 1 hour with the following primary antibodies; anti-RAX (rabbit polyclonal, 1:500; Abcam), anti-Chx10 (sheep polyclonal, 1:100; Exalpha Biologicals, Inc.), anti-Crx (mouse monoclonal, 1:500; Abnova) and anti-Recoverin (rabbit polyclonal, 1:1000; Millipore).

After washing with PBS, specimens were incubated for 30 minutes at room temperature with one of the following secondary antibodies: Rhodamine Red-X-conjugated Donkey Anti-Mouse IgG; Rhodamine Red-X-conjugated Donkey Anti-Rabbit IgG; Cy3-conjugated Donkey anti-Sheep IgG (1:100; all from Jackson ImmunoResearch). Nuclei were counterstained with 4,6-diamidino-2-phenylindole (DAPI)-containing mounting medium (Vector Laboratories, USA). The specimens were visualized with an Olympus BX61 fluorescent microscope (Olympus, Hamburg, Germany). For the images presented herein, an Olympus BX61 microscope equipped with a DP70 digital camera was used.

FIG. 59A shows an image of hESC-derived photoreceptor progenitor cells stained in vitro with anti-RAX antibodies (red) and with DAPI nuclear counterstaining (blue). FIG. 59B shows an image of hESC-derived photoreceptor progenitor cells stained in vitro with anti-RAX antibodies (red) and GFP expression by the cells (green). FIG. 60A shows an image of hESC-derived photoreceptor progenitor cells stained in vitro with anti-Chx10 antibodies (red) and DAPI nuclear counterstaining (blue). FIG. 60B shows an image of hESC-derived photoreceptor progenitor cells stained in vitro with anti-Chx10 antibodies (red) and GFP expression by the cells (green). FIG. 61A shows an image of hESC-derived photoreceptor progenitor cells stained in vitro with anti-Crx antibodies (red) with DAPI nuclear counterstaining (blue). FIG. 61B shows an image of hESC-derived photoreceptor progenitor cells stained in vitro with anti-Crx antibodies (red) and GFP expression by the cells (green). FIG. 62A and FIG. 62C show images of hESC-derived photoreceptor progenitor cells stained in vitro with anti-Recoverin (red) with DAPI nuclear counterstaining (blue). FIGS. 62B and 62D show images of hESC-derived photoreceptor progenitor cells stained in vitro with anti-Recoverin (red). As shown by the images, the expression of RAX, Chx10 and Crx was demonstrated in numerous cells. Cells showing expression of Recoverin, a marker seen later in photoreceptor development, can also be seen. Recoverin is expressed by immature rods and cones.

Example 3

Engraftment of Transplanted hESC-Derived Photoreceptor Progenitor Cells hESC-derived photoreceptor progenitors were engineered to express GFP, as shown in FIG. 63A and magnified further in FIG. 63B., to facilitate the identification of transplanted cells within host tissues. Constitutive expression of eGFP was accomplished by genetic modification of the hESCs with lentiviral vector. At the stage of hESCs expansion on cord feeders, the cells were infected with a lentiviral vector, according to Gropp et al., 2003 Stable genetic modification of human embryonic stem cells by lentiviral vectors. Mol Ther February; 7(2):281-7 PMID:12597917. In infected hESCs, constitutive eGFP expression is driven by the human EF1α promoter.

For intraocular injection, adult rodents were anesthetized with Ketamine HCl (100 mg/kg), injected intraperitoneally in combination with the relaxing agent Xylazine (2.0 mg/kg). Local anesthetic drops (Benoxinate HCl 0.4%) were administered to the eye before the procedure.

The anesthetized animals were positioned in a lateral position with the nose toward the surgeon. All procedures were performed under visualization of a dissecting microscope. A 3-4 mm conjunctival incision was made by scissors parallel and approximately 2 mm posterior to the limbus. The sclera was penetrated with a 30 G needle and a tunnel reaching the subretinal space was made, avoiding penetration of the retina. For reduction of intraocular pressure, an anterior chamber paracentesis was performed with a 30 G needle. Subsequently, a 33 G blunt needle connected to a Hamilton syringe was inserted through the previously created tunnel into the subretinal space and 1-3 μl of photoreceptor progenitor cell suspension was injected at a concentration of 50,000-100,000 cells per μl. After retracting the needle, the conjunctiva was returned to its original position covering the point of entry. The subretinal transplantation procedure is shown in FIG. 64. Subretinal bleb formation was confirmed by direct visualization, as shown in FIG. 65.

After induction of differentiation in vitro with NIC, bFGF and CHIR, cells were transplanted to the subretinal space. As illustrated in FIG. 66, immunohistochemical staining with anti-GFP antibody (green) showed engraftment of the transplanted cells in the subretinal space ("subretinal graft") with migration into the different retinal layers. Sporadic GFP-positive cells were incorporated in the Outer Nuclear Layer (photoreceptors) (ONL, arrow). Nuclei were counterstained with DAPI (blue). The image shown in FIG. 66 is from an eye enucleated 4 weeks post-transplantation.

After enucleation, eyes were fixed in Davidson solution, embedded in paraplast and sectioned at 4 μm sections. Sections were de-parafinized in xylene and dehydrated in graded alcohols, rinsed with phosphate-buffered saline (PBS, pH 7.4), and incubated with 10 mM citrate buffer (pH 6.0) at 125° C. for 10 minutes. After washing with PBS, specimens were blocked for 1 hour at room temperature with PBS solution containing 1% bovine serum albumin, 0.1% TRITON™-x100, and 3% normal donkey serum. Subsequently, sections were incubated for 24 hours at 4° C. in a humidified chamber with one of the following primary antibodies: anti-GFP (FITC or TRITC-conjugated, 1:100; Santa Cruz Biotechnology, Inc.), anti-rhodopsin (mouse monoclonal, 1:100; Lab Vision Corporation), anti-blue-sensitive opsin (goat polyclonal, 1:75; Santa Cruz Biotechnology, Inc.), anti-red/green opsin (rabbit polyclonal, 1:100; Chemicon International). After washing in PBS, specimens were incubated for 1 hour at room temperature with one of the following secondary antibodies: DY-LIGHT™ 488 (or 549) AFFINIPURE™ Donkey Anti-Mouse IgG; DY-LIGHT™ 488 (or 549) AFFINIPURE™ Donkey Anti-Rabbit IgG; Rhodamine Red-X-conjugated donkey anti-goat IgG (1:250; all from Jackson ImmunoResearch). Nuclei were counterstained with 4,6-diamidino-2-phenylindole (DAPI)-containing mounting medium (Vector Laboratories, USA). To determine the specificity of the antigen-antibody reaction, corresponding negative controls were performed. A fluorescence microscope and/or a confocal microscope was then used to image the stained sections. For the images presented herein, an Olympus BX41 microscope equipped with a DP70 digital camera was used.

As shown in FIG. 67, a large number of transplanted cells (green) can be seen in the subretinal graft expressing the rod-photoreceptor-specific marker rhodopsin (red), 7 weeks post transplantation. Host rod photoreceptors also express rhodopsin, but not GFP. Nuclei were counterstained with DAPI (blue). FIG. 68 shows transplanted cells (green) in a subretinal graft expressing the cone-photoreceptor-specific marker red/green opsin (red, arrows), at 7 weeks post-transplantation. Nuclei were counterstained with DAPI (blue).

FIG. 69, FIG. 70 and FIG. 71 are images of stained subretinal grafts comprising GFP-expressing, hESC-derived photoreceptor progenitor cells that were differentiated using NIH prior to transplantation. The images were taken 4 to 6 weeks after transplantation. As shown in FIG. 69 and FIG. 70, numerous cells within the graft co-expressed rhodopsin (red). Transplanted GFP and rhodopsin co-expressing cells can also be seen within the ONL. FIG. 71 shows co-staining of GFP expressing cells and the cone marker red/green opsin within the subretinal graft. These images show abundant cells within the graft that are expressing red/green opsin. These results demonstrate that the transplanted hESC-derived photoreceptor progenitor cell grafts are capable of survival, engraftment, migration, and differentiation into cells expressing markers of mature rods and cones photoreceptors. Cones are the photoreceptor cells that are responsible for day light fine visual capability and that rods are responsible for night vision. Cones are highly abundant in the macula the area in the retina essential for fine and high resolution visual capability.

From the description herein, it will be appreciated that that the present disclosure encompasses multiple embodiments which include, but are not limited to, the following:

A method of generating photoreceptor cells, the method comprising (a) culturing stem cells in a medium comprising nicotinamide under conditions that give rise to photoreceptor cells.

The method of any previous embodiment, wherein the medium comprises at least 0.5 mM nicotinamide.

The method of any previous embodiment, further comprising (b) culturing cells generated in step (a) in a medium comprising at least one agent or a combination of agents selected from the group consisting of a GSK3 inhibitor, a Wnt inhibitor, bFGF, HSA, or IGF.

The method of any previous embodiment, further comprising isolating photoreceptor cells following the culturing of step (b).

The method of any previous embodiment, further comprising expanding said cells following said culturing of step (b).

The method of any previous embodiment, wherein said culturing of step (a) is effected under non-adherent conditions.

The method of any previous embodiment, wherein said culturing of step (b) is effected under non-adherent conditions.

The method of any one of any previous embodiment, wherein said medium of step (b) comprises one or more of:
(i) nicotinamide and Wnt inhibitor;
(ii) nicotinamide and bFGF;
(iii) nicotinamide and IGF;
(iv) nicotinamide, IGF and a GSK3 inhibitor
(v) nicotinamide, bFGF and Wnt inhibitor
(vi) nicotinamide, Wnt inhibitor and HSA (vii) nicotinamide, bFGF, and HSA
(viii) nicotinamide, bFGF, Wnt inhibitor and HSA; or
(ix) nicotinamide, and HSA.

The method of any previous embodiment, wherein said culturing of step (a) is effected for at least 3 days.

The method of any previous embodiment, wherein said culturing of step (b) is effected for at least one week.

The method of any previous embodiment, wherein said medium of step (b) is substantially devoid of activin A.

The method of any previous embodiment, wherein said medium of step (b) is substantially devoid of a member of the TGFβ superfamily.

The method of any previous embodiment being effected in the absence of a member of the TGFbeta superfamily which allows differentiation into said photoreceptor cells.

The method of any previous embodiment, wherein said stem cells are cultured in a feeder cell conditioned medium prior to the culturing of step (a).

The method of any previous embodiment, wherein said stem cells are cultured in a feeder-free system on laminin prior to the culturing of step (a).

The method any previous embodiment, further comprising cryopreserving said photoreceptor cells following step (b).

The method of any previous embodiment, wherein said cryopreserving is effected in a medium selected from the group consisting of 90% Human Serum/10% DMSO, CRYOSTOR™ 10%, CRYOSTOR™ 5%, CRYOSTOR™ 2%, STEM-CELLBANKER™ and PRIME-XV™ FreezIS.

The method of any previous embodiment, wherein said stem cells comprise human embryonic stem cells (ESCs) or induced pluripotent stem cells (iPSCs).

The method of any previous embodiment, wherein said medium of step (a) is substantially devoid of Wnt inhibitor, bFGF, HSA, IGF and/or GSK3 inhibitor.

The method of any previous embodiment, wherein said GSK3 inhibitor comprises CHIR.

The method of any previous embodiment, wherein said Wnt inhibitor comprises endo-IWR1.

The method of any previous embodiment, wherein said non-adherent conditions comprise a non-adherent culture plate.

The method of any previous embodiment, wherein said non-adherent conditions comprise a non-adherent substrate.

The method of any previous embodiment, wherein said feeder cell conditioned medium comprises human cord fibroblast conditioned medium.

The method of any previous embodiment, further comprising transplanting the photoreceptor cells in the subretinal space of the eye.

The method of any previous embodiment, wherein said photoreceptor cells are transplanted in a suspension, or as a monolayer of cells immobilized on a matrix or a substrate.

A method of generating photoreceptor cells comprising:
(a) culturing a population of human pluripotent stem cells in a medium comprising at least 0.5 mM nicotinamide, wherein said culture does not comprise any member of the TGFβ superfamily at a concentration which allows differentiation into said photoreceptor cells; and
(c) isolating said photoreceptor cells from retinal pigmented epithelial (RPE) cells, thereby generating the photoreceptors.

A population of photoreceptor cells obtainable according to the method of any previous embodiment.

The method of any previous embodiment, wherein said retinal disease or disorder is selected from at least one of retinitis pigmentosa, lebers congenital amaurosis, hereditary or acquired macular degeneration, age related macular degeneration (AMD), Best disease, retinal detachment, gyrate atrophy, choroideremia, pattern dystrophy, RPE dystrophies, Stargardt disease, RPE and retinal damage due to damage caused by any one of photic, laser, inflammatory, infectious, radiation, neovascular or traumatic injury.

A method of treating a retinal disease or disorder in a subject in need thereof comprising, administering a therapeutically effective amount of the population of photoreceptor cells of any previous embodiment to the subject thereby treating the retinal disease or disorder.

A method of treating a retinal disease or disorder, the method comprising administering to a subject in need thereof an effective amount of photoreceptor cells or a preparation of photoreceptor cells obtained by a method comprising (a) culturing stem cells in a medium comprising nicotinamide under conditions that give rise to photoreceptor cells.

The method of any previous embodiment, wherein the medium comprises at least 0.5 mM nicotinamide.

The method of any previous embodiment, further comprising (b) culturing cells generated in step (a) in a medium comprising at least one agent selected from the group consisting of a GSK3 inhibitor, a Wnt inhibitor, bFGF, HSA and or IGF.

The method of any previous embodiment, further comprising isolating photoreceptor cells following the culturing of step (b).

The method of any previous embodiment, wherein said culturing of step (a) or step (b) is effected under non-adherent conditions.

The method of any previous embodiment, wherein said medium of step (b) comprises one or more of:
(i) nicotinamide and Wnt inhibitor;
(ii) nicotinamide and bFGF;
(iii) nicotinamide and IGF;
(iv) nicotinamide, IGF and a GSK3 inhibitor
(v) nicotinamide, bFGF and Wnt inhibitor
(vi) nicotinamide, Wnt inhibitor and HSA
(vii) nicotinamide, bFGF, and HSA
(viii) nicotinamide, bFGF, Wnt inhibitor and HSA; or
(ix) nicotinamide, and HSA.

The method of any previous embodiment, wherein said stem cells comprise human embryonic stem cells (ESCs) or induced pluripotent stem cells (iPSCs).

The method of any previous embodiment, wherein said administering is effected at the subretinal space of the eye.

The method of any previous embodiment, wherein said photoreceptor cells are administered in a suspension, or as a monolayer of cells immobilized on a matrix or a substrate.

The method of any previous embodiment, further comprising isolating the photoreceptor cells from the culture.

The method of any previous embodiment, wherein the photoreceptor cells are cryopreserved prior to administering.

The method of any previous embodiment, wherein the photoreceptor cells comprise cone and rod cells.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of generating a population of photoreceptor cells, the method comprising (a) culturing, for 3 days to 2 weeks, human embryonic stem cells in a medium comprising a differentiation agent, wherein said differentiation agent comprises at least 0.5 mM nicotinamide, under conditions that generate differentiating cells, and (b) culturing the differentiating cells generated in step (a) in a medium comprising at least 0.5 mM nicotinamide and a combination of at least three agents selected from a glycogen synthase kinase-3 (GSK3) inhibitor, a Wnt inhibitor, basic fibroblast growth factor (bFGF), human serum albumin (HSA), or insulin growth factor (IGF) for a period of time to generate a population of photoreceptor cells, wherein at least 70% of the population expresses neural retina-specific leucine zipper protein (Nrl), wherein the method is effected in the absence of a member of the transforming growth factor beta (TGFβ) superfamily in an amount which effects differentiation into said population of photoreceptor cells.

2. The method of claim 1, further comprising isolating the photoreceptor cells following the culturing of step (b).

3. The method of claim 1, further comprising expanding said photoreceptor cells following said culturing of step (b).

4. The method of claim 1, wherein said culturing of step (a) is effected under non-adherent conditions.

5. The method of claim 1, wherein said culturing of step (b) is effected under non-adherent conditions.

6. The method of claim 1, wherein said medium of step (b) comprises:

bFGF, Wnt inhibitor and HSA;

(ix).

7. The method of claim 1, wherein said human embryonic stem cells are cultured in a feeder cell conditioned medium prior to the culturing of step (a).

8. The method of claim 1, wherein said human embryonic stem cells are cultured in a feeder-free system on laminin prior to the culturing of step (a).

9. The method of claim 1, wherein said medium of step (a) is devoid of Wnt inhibitor, bFGF, HSA, IGF and/or GSK3 inhibitor.

10. The method of claim 7, wherein said feeder cell conditioned medium comprises human cord fibroblast conditioned medium.

* * * * *